United States Patent [19]
Huang et al.

[11] Patent Number: 6,130,333
[45] Date of Patent: Oct. 10, 2000

[54] BICYCLIC IMIDAZOLYL DERIVATIVES AS PHOSPHODIESTERASE INHIBITORS, PHARMACEUTICAL COMPOSITIONS AND METHOD OF USE

[75] Inventors: Horng-Chih Huang, Chesterfield, Mo.; Timothy S. Chamberlain, Des Plaines, Ill.; Steven Lynn Settle, Wildwood; William Dean Joy, Creve Coeur, both of Mo.; Ned R. Siegel, Belleville, Ill.; Leslie D. Bell, Chesterfield, Mo.

[73] Assignee: Monsanto Company, St. Louis, Mo.

[21] Appl. No.: 09/200,863

[22] Filed: Nov. 27, 1998

[51] Int. Cl.[7] ............ C07D 235/04; C07D 401/06; C07D 471/02; A61K 81/437; A61K 31/443; A61K 31/4184; A61N 27/06

[52] U.S. Cl. ............ 546/118; 514/303; 514/341; 514/394; 546/273.4

[58] Field of Search ............ 548/305.1; 546/118, 546/273.4; 514/394, 341, 303

[56] References Cited

U.S. PATENT DOCUMENTS

| | | | |
|---|---|---|---|
| 3,257,204 | 6/1966 | Süs et al. | 96/1.5 |
| 3,953,600 | 4/1976 | Houlihan | 424/273 |
| 4,421,755 | 12/1983 | Benedikter et al. | 424/256 |
| 5,334,598 | 8/1994 | Bagley et al. | 514/303 |
| 5,576,322 | 11/1996 | Takase et al. | 514/260 |

FOREIGN PATENT DOCUMENTS

| | | |
|---|---|---|
| 1 137 625 | 10/1962 | Germany . |
| 2305339 | 3/1973 | Germany . |
| 123 053 | 11/1976 | Germany . |
| 45-039541 | 12/1970 | Japan . |
| 1 200 907 | 8/1970 | United Kingdom . |

OTHER PUBLICATIONS

N.V. Subra Rao, et al., "Studies in the Formation of Heterocyclic Rings Containing Nitrogen Part I. Condensation of o–Phenylenediamine with Aromatic Aldehydes", Proc. Indian Acad. Sci. 43A, 173–80 (1956).

N.V. Subra Rao, et al., "Studies in the Formation of Heterocyclic Rings Containing Nitrogen Part VI. Condensation of 4–Chloro–o–Phenylenediamine with Aromatic Aldehydes", Proc. Indian Acad. Sci., vol. XLVIII, Sec. A, 256–262 (1959).

N.V. Subra Rao, et al., "Studies in the Formation of Heterocyclic Rings Containing Nitrogen Part VII. Condensation of 4–Nitro–o–Phenylenediamine with Aromatic Aldehydes", Proc. Indian Acad. Sci., vol. XLIX, Sec. A, 193–199 (1959).

L.N. Pushkina, et al., "II. Syntheses of Benzimidazoles for Studying their Scintillation Properties", J. of Gen. Chem. of the U.S.S.R., vol. 32, 2585–2592 (1962).

K. Kondal Reddy, et al. "Synthesis of Some 1–Benzyl Benziminazoles", Indian J. Chem., vol. 1, 96–98 (1963).

V. Veeranagaiah, et al., "Studies in the Formation of Heterocyclic Rings Containing Nitrogen: Part XII—Pyrolysis of 1,3–Dibenzyl–2–substituted Benzimidazolines & Preparation of I–Benzyl–2–substituted Benzimidazoles", Indian J. Chem., vol. 7, 776–778 (1969).

V. Veeranagaiah, et al., "Studies in the Formation of Heterocyclic Rings Containing Nitrogen: Part XVIII—Pyrolysis of 1,3–Dibenzyl–2–substituted–5–methylbenzimidazolines", Indian J. Chem., vol. 12, 346–348 (1974).

(List continued on next page.)

*Primary Examiner*—Floyd D. Higel
*Attorney, Agent, or Firm*—Fitzpatrick, Cella, Harper & Scinto

[57] ABSTRACT

The present invention provides for compounds having the following Formulae I–III,

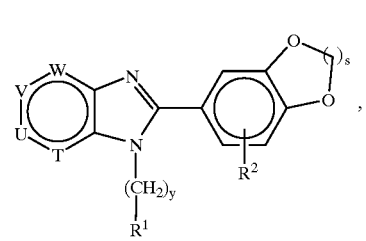

Formula I

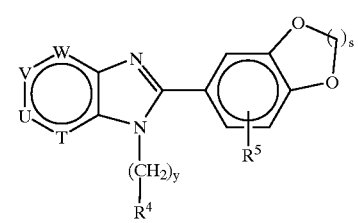

Formula II and

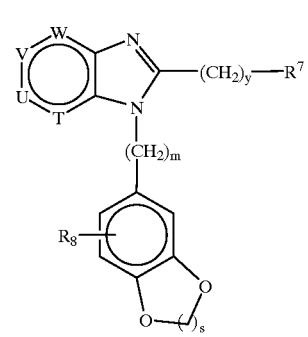

Formula III The compounds of the present invention are useful in the treatment of a variety of disease such as glaucoma, sexual dysfunction, asthma and cardiovascular disorders such as stable-, unstable- and variant-angina, hypertension, pulmonary hypertension, congestive heart failure, atherosclerosis, and thrombosis.

4 Claims, 1 Drawing Sheet

OTHER PUBLICATIONS

V. Veeranagaiah, et al., "Studies in the Formation of Heterocyclic Rings Containing Nitrogen: Part XX—Products of Pyrolysis of 1,3–Dibenzyl–2–substituted–5–chlorobenzimidazolines", Proc. Indian Acad. Sci., 230–235 (1974).

P. Satyanarayana Reddy, et al., "Studies in the Formation of Heterocyclic Rings Containing Nitrogen: Part XXI—Synthesis of $N^1$, $N^2$–differently substituted benzimidazolines", Proc. Indian Acad. Sci., vol. 81A, No. 3, 124–131 (1975).

C.V. Chalapathy Rao, et al., "Condensation of 3–Methyl-1–o–phenylenediamine with Aromatic Aldehydes", Indian J. Chem., vol. 17B, 566–568 (1979).

C.V. Chalapathy Rao, et al., "Pyrolysis of $N^1$, $N^3$–Disubstituted 5–Methyl–& 5–Chlorobenzimidazolines", Indian J. Chem., vol. 19B, 967–969 (1980).

Chemical Abstracts: Registry No. 150452–72–5 "1H–Benzomidazole, 1–(1,3–benzodioxol–5–ylmethyl)–6–chloro–2–(1H–imidazol–1–yl)–(9CI)." (1994).

Chemical Abstracts: Registry No. 121497–23–2 "3,5–Pyridinedicarboxylic acid, 4–[2–(1,3–benzodioxol–5–yl)–(1–1,3–benzodioxol–5–ylmethyl)–1H–benzimidazol–6–yl]–1,4–dihydro–2,6–dimethyl, dimethyl ester (9CI)." (1994).

Chemical Abstracts: Registry No. 116636–82–9 "Benzimidazole, 5–chloro–2–(3,4–methylenedioxylphenyl)–1–piperonyl–(6CI)." (1994).

Chemical Abstracts: Registry No. 116601–35–5 "Benzimidazole, 2–(3,4–methylenedioxyphenyl)–6–nitro–1–piperonyl–(6CI)." (1994).

Chemical Abstracts: Register No. 114223–08–4 "Benzimidazole, 6–methyl–2–(3,4–methylenedioxyphenyl)–1–piperonyl–(6CI)." (1994).

Chemical Abstracts: Registry No. 112351–06–1 "Benzimidazole, 2–(3,4–methylenedioxyphenyl)–1–piperonyl–(6CI)." (1994).

Chemical Abstracts: Registry No. 94963–80–1 "Benzimidazole, 1–benzyl–2–[3,4–(methylenedioxy)phenyl]–(7CI)." (1994).

Chemical Abstracts: Registry No. 94878–73–6 "Benzimidazole, 1–benzyl–2–[3,4–(methylenedioxy)phenyl]–5–nitro–(7CI)." (1994).

Chemical Abstracts: Registry No. 77314–32–0 "1H–Benzimidazole, 2–(1,3–benzodioxol–5–yl)–6–chloro–1–methyl–(9CI)." (1994).

Chemical Abstracts: Registry No. 77314–25–1 "1H–Benzimidazole, 2–(1,3–benzodioxol–5–yl)–1,6–dimethyl–(9CI)." (1994).

Chemical Abstracts: Registry No. 76424–16–3 "Benzenamine, 2–[1–(1,3–benzodioxol–5–ylmethyl)–1H–benzimidazol–2–yl]–(9CI)." (1994).

Chemical Abstracts: Registry No. 76424–15–2 "1H–Benzimidazole, 1–(1,3–benzodioxol–5–ylmethyl)–2–(2–chlorophenyl)–(9CI)." (1994).

Chemical Abstracts: Registry No. 76424–14–1 "1H–Benzimidazole, 1–(1,3–benzodioxol–5–ylmethyl)–2–phenyl–(9CI)." (1994).

Chemical Abstracts: Registry No. 76424–13–0 "1H–Benzimidazole, 1–(1,3–benzodioxol–5–ylmethyl)–2–ethyl–(9CI)." (1994).

Chemical Abstracts: Registry No. 76424–12–9 "1H–Benzimidazole, 1–(1,3–benzodioxol–5–ylmethyl)–2–methyl–(9CI)." (1994).

Chemical Abstracts: Register No. 76145–62–5 "3H–Naphth[1,2–d]imidazole, 2–(1,3–benzodioxol–5–yl)–3–methyl–(9CI)." (1994).

Chemical Abstracts: Registry No. 75133–99–2 "1H–Benzimidazole, 2–(1,3–benzodioxol–5–ylmethyl)–4–methyl–(9CI)." (1994).

Chemical Abstracts: Registry No. 67482–39–7 "3H–Imidazo[4,5–b]pyridine, 3–(1,3–benzodioxol–5–yl)–2–phenyl–(9CI)." (1994).

Chemical Abstracts: Registry No. 53886–95–6 "1H–Benzimidazole, 2–(1,3–benzodioxol–5–yl)–6–chloro–1–(phenylmethyl–(9CI)." (1994).

Chemical Abstracts: Registry No. 53811–82–8 "1H–Benzimidazole, 2–(1–3–benzodioxol–5–yl)–5–methyl–1–(phenylmethyl)–(9CI)." (1994).

Chemical Abstracts: Registry No. 53811–67–9 "1H–Benzimidazole, 2–(1,3–benzodioxol–5–yl)–6–methyl–1–(phenylmethyl–(9CI)." (1994).

Chemical Abstracts: Registry No. 53703–87–0 "1H–Benzimidazole, 2–(1,3–benzodioxol–5–yl)–5–chloro–1–(phenylmethyl)–(9CI)." (1994).

Chemical Abstracts: Registry No. 32286–72–9 "Benzimidazole, 1–[3–(dimethylamino)propyl]–2–[3,4–(methylenedioxy)phenyl]–, dihydrochloride (8CI)." (1994).

Chemical Abstracts: Registry No. 10200–56–3 "Benzimidazole, 1–5–dimethyl–2–[3,4–(methylenedioxy)phenyl]–(7CI)." (1994).

Chemical Abstracts: Registry No. 3653–07–4 "Benzimidazolium, 1,3–dimethyl–2–[3,4–(methylenedioxy)phenyl]–, iodide (8CI)." (1994).

Chemical Abstracts: Register No. 3653–02–9 "Benzimidazolium, 1,3–dimethyl–2–[3,4–(methylenedioxy)phenyl]–, chloride (8CI)." (1994).

SciFinder, Registry No. 32286–72–9, "Benzimidazole, 1–[3–dimethylamino)propyl]–2–[3,4–(methylenedioxy)phenyl]–, dihydrochloride (8CI)." (1994).

Abstract; JP70039541, "Benzimidazole derivatives having CNS depressant and stimulant, sedative, anti–inflammatory." (1994).

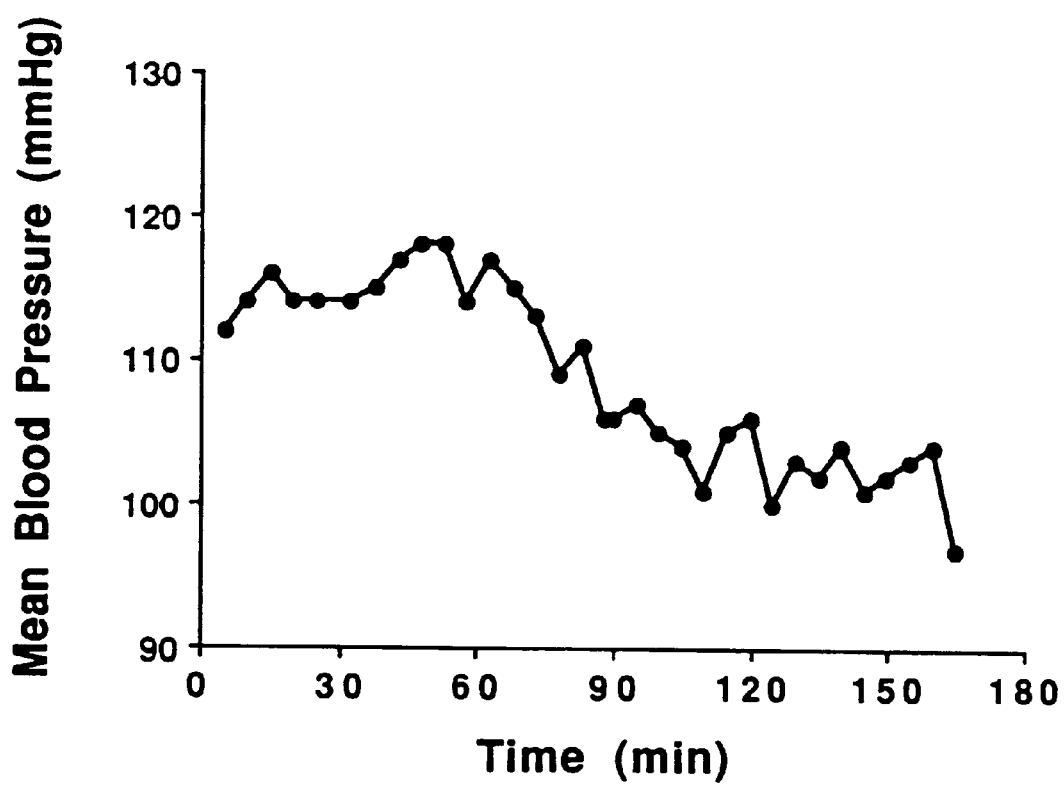

BICYCLIC IMIDAZOLYL DERIVATIVES AS PHOSPHODIESTERASE INHIBITORS, PHARMACEUTICAL COMPOSITIONS AND METHOD OF USE

BACKGROUND OF THE INVENTION

1. Field of the Invention

This invention relates to a series of benzimidazole, pyridineimidazole, pyrazineimidiazole pyrimidineimidazole, pyridazineimidazole, and triazineimidazole derivatives which are selective inhibitors of the cyclic guanosine 3',5'-monophosphate phosphodiesterase enzyme ("cGMP PDE"), having utility in a variety of therapeutic areas including, for example, the treatment of cardiovascular disorders such as stable-, unstable- and variant-angina, hypertension, pulmonary hypertension, congestive heart failure, atherosclerosis, thrombosis, glaucoma, sexual dysfunction, asthma (all pathological states which result in the elevation of intracellular levels of GMP) and any other disease condition related to the inhibition of cGMP PDE.

2. Related Background Art

Cyclic nucleotides are involved in regulating the activity of many cells in the airways, including pro-inflammatory, immunocompetent cells such as macrophages, eosinophils, mast cells and lymphocytes, and airway smooth muscle. Cyclic nucleotides that have been identified include cyclic adenosine 3',5'-monophosphate ("cAMP") and cyclic guanoside 3',5'-monophosphate ("cGMP"). Cyclic nucleotides are inactivated by the action of cyclic nucleotide phosphodiesterase enzymes ("PDEs"). Multiple molecular forms of PDEs are present in mammalian cells. At least five different families have been identified. These families differ with respect to substrate specificity, intracellular location, sensitivity to inhibitors, and mode of regulation.

Cyclic guanoside 3',5'-monophosphate phosphodiesterase ("cGMP PDE") is responsible for inactivation of cGMP by catalyzizing the hydrolysis of 3'-ribose phosphate bond of cGMP as shown in Scheme 1.

Scheme 1.
Hydrolysis of the 3'-ribose phosphate bond
of cGMP by cGMP PDE resulting in the
formation of GMP.

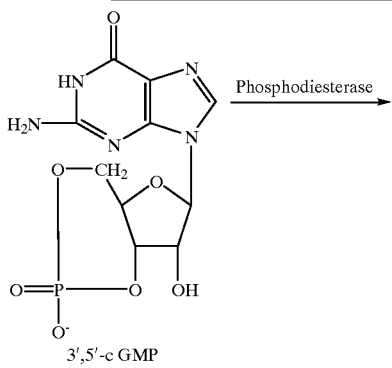

3',5'-c GMP

Phosphodiesterase

-continued

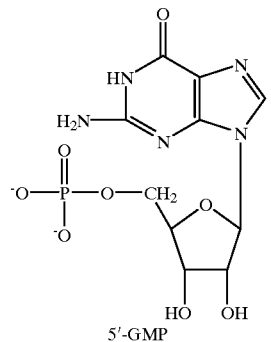

5'-GMP

Scheme 1. Hydrolysis of the 3'-ribose phosphate bond of cGMP by cGMP PDE resulting in the formation of GMP.

Selective inhibition of cGMP PDE results in elevation of cGMP levels, which in turn can give rise to beneficial anti-platelet, anti-neutrophil, anti-vasospastic and vasodilatory activity. Thus such inhibitors of the cGMP PDE have utility in the treatment of diseases such as stable-, unstable- and variant-angina, hypertension, pulmonary hypertension, congestive heart failure, atherosclerosis, thrombosis, glaucoma, impotence, asthma (all pathological states which result in the elevation of intracellular levels of GMP) and any other disease condition related to the inhibition of cGMP PDE. It has been shown that selective inhibitors of cGMP PDE lower mean arterial blood pressure and promote sodium excretion in an anesthetized rat (E. G. McMahon et al., *J. Pharmacol. Exp. Ther.* 251, 1000–1005, 1989). Accordingly, inhibitors of cGMP PDE are potentially potent drugs for use in treating a wide variety of circulatory type disorders.

Some efforts have been made to develop cGMP PDE inhibitors. For example, a number of pyrido[3,2-d] pyrimidin-4-one derivatives have been disclosed in the prior art as cGMP PDE inhibitors. In particular, PCT International Publication No. WO 94/05661 discloses a series of pyrido [3,2-d]pyrimidin-4-ones containing a 2,5-disubstituted phenyl moiety at the 2 position of the pyrido[3,2-d]pyrimidin-4-one bicyclic system as selective inhibitors of cGMP PDE over cAMP PDE. In European patent application No. EP-A-0347146 another series of pyrido[3,2-d]pyrimidin-4-one phosphodiesterase inhibitors having a monosubstituted phenyl moiety at the 2-position of the hetrocyclicbicyclic ring system were disclosed. In U.S. Pat. No. 5,576,322 a series of 2,4-diaminoquinazoline compounds are disclosed as cGMP PDE inhibitors.

The identification of additional potent and selective cGMP PDE inhibitors is highly desirable. This invention provides a series of benzimidazole, pyridineimidazole, pyrazineimidiazole pyrimidineimidazole, pyridazineimidazole, and triazineimidazole derivatives which are selective inhibitors of cGMP PDE. The disclosed cGMP PDE inhibitors are useful in the treatment of a variety of cardiovascular disorders.

SUMMARY OF THE INVENTION

The invention relates to compounds having a structure of Formula I,

Formula I

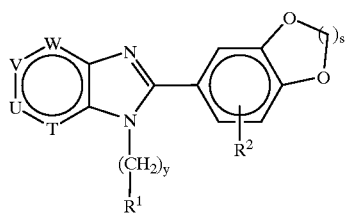

or a pharmaceutically acceptable salt thereof;
wherein y is an integer from 0 to 6;
wherein s is an integer from 1 to 3;
wherein $R^1$ is selected from the group consisting of alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl, heterocycle, bicyclic aryl, heteroaryl and aryl, and wherein alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl and heterocycle may be optionally substituted by one or more substituent(s) independently selected from the group consisting of alkyl, alkyl sulfonyl, alkenyl, alkynyl, amino, hydroxy and alkoxy, and wherein bicyclic aryl, heteroaryl and aryl may be optionally substituted by one or more substituent(s) independently selected from the group consisting of halo, nitro, alkyl, alkyl sulfonyl, alkenyl, alkynyl, amino, hydroxy, alkoxy, alkoxycarbonyl, and —O—$(CH_2)_p$—O—, wherein p is an integer from 1 to 3 and the oxygen atoms are bonded to adjacent carbons;
wherein $R^2$ is selected from the group consisting of hydrido, hydroxy, halo, nitro, alkyl, alkyl sulfonyl, alkoxy, alkenyl, alkynyl and amino; and wherein T, U, V, and W are each independently N or $CR^3$ with the proviso that at least one of T, U, V, and W is $CR^3$, wherein each $R^3$ when present is independently selected from the group consisting of hydrido, hydroxy, halo, nitro, alkyl, alkyl sulfonyl, alkoxy, alkenyl, alkynyl and amino, and with the proviso that Formula I is not Benzimidazole-2-(3,4-methylenedioxyphenyl)-5-methyl, Benzimidazole-1-piperonyl-2-(3,4-methylenedioxyphenyl)-5-chloro, Benzimidazole-1-piperonyl-2-(3,4-methylenedioxyphenyl)-6-nitro, Benzimidazole-1-piperonyl-2-(3,4-methylenedioxyphenyl)-6-methyl, Benzimidazole-1-piperonyl-2-(3,4-methylenedioxyphenyl), Benzimidazole-2-(3,4-methylenedioxyphenyl)-5-nitro, Benzimidazole-2-(3,4-methylenedioxyphenyl)-6-nitro, Benzimidazole-2-(3,4-methylenedioxyphenyl)-5-chloro, Benzimidazole-2-(3,4-methylenedioxyphenyl)-6-chloro, 1H-Purine-8-(2,3-dihydro-1,4-benzodioxin-6-yl), 1H-Imidazol-[4,5-c]pyridine-2-(2,3-dihydro-1,4-benzodioxin-6-yl), 1H-Purine-8-(2,3-dihydro-1,4-benzodioxin-6-yl)-monohydrochloride, 1H-Imidazol[4,5-c]pyridine-2-(2,3-dihydro-1,4-benzodioxin-6-yl)-monohydrochloride, Benzimidazole-1-benzyl-2-(3,4-methylenedioxyphenyl), Benzimidazole-1-benzyl-2-(3,4-methylenedioxyphenyl)-5-nitro, Benzimidazole-1-methyl-2-(3,4-methylenedioxyphenyl)-6-chloro, Benzimidazole-1,6-dimethyl-2-(3,4-methylenedioxyphenyl), Benzimidazole-2-(3,4-methylenedioxyphenyl)-4-methyl, Benzimidazole-1-(3,4-methylenedioxyphenyl)-2-(3,4-methylenedioxyphenyl)-4-methyl, Benzimidazole-1-benzyl-2-(3,4-methylenedioxyphenyl)-6-chloro, Benzimidazole-1-benzyl-2-(3,4-methylenedioxyphenyl)-5-methyl, Benzimidazole-1-benzyl-2-(3,4-methylenedioxyphenyl)-6-methyl, Benzimidazole-1-benzyl-2-(3,4-methylenedioxyphenyl)- 5-chloro, Benzimidazole-1,5-dimethyl-2-(3,4-methylenedioxyphenyl), Benzimidazole-1-methyl-2-(3,4-methylene dioxyphenyl), Benzimidazole-2-(3,4-methylenedioxy phenyl), Benzimidazole-1-methyl-2-(3,4-methylenedioxy phenyl)-5-methyl, Benzimidazole-1-(3,4-methylenedioxy phenylmethyl)-2-(3,4-methylenedioxy phenyl)-5-methyl, or Benzimidazole-1-(3,4-methylenedioxyphenylmethyl)-2-(3,4-methylenedioxyphenyl)-5-chloro.

The invention also relates to compounds having a structure of Formula II,

Formula II

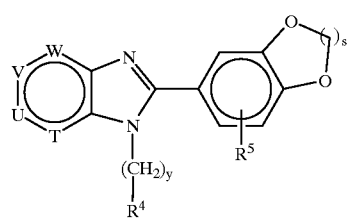

or a pharmaceutically acceptable salt thereof;
wherein y is an integer from 0 to 6;
wherein s is an integer from 1 to 3;
wherein $R^4$ is selected from the group consisting of alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl, heterocycle, bicyclic aryl, heteroaryl and aryl, any of which may be optionally substituted by one or more substituent(s) independently selected from the group consisting of alkyl, alkyl sulfonyl, alkenyl, alkynyl, amino, hydroxy and alkoxy, with the exception that alkenyl is not amino substituted and wherein bicyclic aryl, aryl and heteroaryl may also be optionally substituted by one or more substituent(s) independently selected from the group consisting of halo, nitro, alkoxycarbonyl and —O—$(CH_2)_p$—O—, wherein p is an integer from 1 to 3 and the oxygen atoms are bonded to adjacent carbons and with the proviso that $(CH_2)_yR^4$ is not methyl and with the proviso that when $R^4$ is substituted alkyl, the substituent is not amino;
wherein $R^5$ is selected from the group consisting of hydrido, hydroxy, halo, nitro, alkyl, alkyl sulfonyl, alkoxy, alkenyl, alkynyl and amino; and
wherein T, U, V, and W are each independently N or $CR^6$ with the proviso that at least one of T, U, V, and W is $CR^6$, with the proviso that when T is N and U, V, and W is $CR^6$, $(CH_2)_yR^4$ is not $C_1$–$C_4$ alkyl, with the proviso that when T is N and U, V, and W are $CR^6$, $(CH_2)_yR^4$ is not benzyl, with the proviso that when W is N and T, U, and V are $CR^6$, $(CH_2)_yR^4$ is not benzyl and with the proviso that when T, U, V and W are all $CR^6$ and S is 1, then $(CH_2)_yR^4$ is not benzyl or 1,3-benzodioxolyl methyl group, wherein each $R^6$ when present is independently selected from the group consisting of hydrido, hydroxy, halo, nitro, alkyl, alkyl sulfonyl, alkoxy, alkenyl, alkynyl and amino and with the proviso that Formula II is not 2-(1,3-benzodioxol- 5-yl)-1-(3,7-dimethyl-6-octen-1-yl)-1H-benzimidazole.

The invention also provides for compounds having the structure of Formula III,

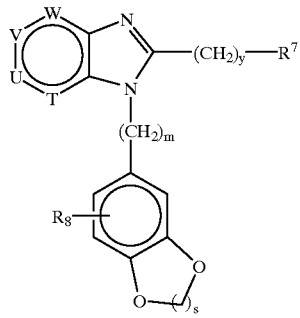

Formula III or a pharmaceutically acceptable salt thereof;
wherein m is an integer from 0 to 3;
wherein y is an integer from 0 to 6;
wherein s is an integer from 1 to 3;
wherein $R^7$ is selected from the group consisting of alkyl, alkoxyalkyl, carboxyalkyl, alkylcarbonyl, arylcarbonyl, alkenyl, alkoxyalkenyl, alkynyl, alkoxyalkynyl, cycloalkyl, cycloalkenyl, heterocycle, bicyclic aryl, heteroaryl and aryl, any of which may be optionally substituted by one or more substituent(s) selected from the group consisting of alkyl, alkyl sulfonyl, alkenyl, alkynyl, amino, hydroxy and alkoxy, and wherein bicyclic aryl, aryl and heteroaryl may also be optionally substituted by one or more substituent(s) selected from the group consisting of halo, nitro, alkoxycarbonyl, and —O—$(CH_2)_p$—O—, wherein p is an integer from 1 to 3 and the oxygen atoms are bonded to adjacent carbons, with the proviso that when m is 1, s is 1, and T, U, V and W are $CR^9$, then $(CH_2)_y R^7$ is not methyl, ethyl or 1,3-benzodioxolyl group;
wherein $R^8$ is selected from the group consisting of hydrido, hydroxy, halo, nitro, alkyl, alkyl sulfonyl, alkoxy, alkenyl, alkynyl and amino; and
wherein T, U, V, and W are each independently N or $CR^9$ and with the proviso that at least one of T, U, V, and W is $CR^9$, wherein each $R^9$ when present is independently selected from the group consisting of hydrido, hydroxy, nitro, alkyl, alkyl sulfonyl, alkoxy, alkenyl, alkynyl and amino and with the proviso that when T is N, M is 0 and S is 1, then $(CH_2)_y R^7$ is not phenyl.

The present invention provides for pharmaceutical compositions comprising a therapeutically effective amount of any of the compounds of Formulae I–III.

The invention also provides for a method of treating glaucoma, sexual dysfunction, asthma and cardiovascular disorders such as stable-, unstable- and variant-angina, hypertension, pulmonary hypertension, congestive heart failure, atherosclerosis, and thrombosis.

BRIEF DESCRIPTION OF THE DRAWING

The FIGURE is a plot of mean blood pressure (mmHg) versus time (min) for anesthetized male Sprague Dawley rats (Charles River Laboratories, Wilmington, Mass.) following administration of a cyclic GMP phosphodiesterase inhibitor of this invention by intraperitoneal injection.

DETAILED DESCRIPTION OF THE INVENTION

For purposes of clarity, the terms and phrases used throughout this specification and the appended claims are defined in the manner set forth directly below. Some of the chemical structures which are presented in this specification have been drawn using the convention which employs lines to represent radicals, which is known by those of skill in the art.

The term "hydrido" denotes a single hydrogen atom (H). This hydrido radical may be attached, for example, to an oxygen atom to form a hydroxyl group or two hydrido radicals may be attached to a carbon atom to form a methylene (—$CH_2$—) radical.

The term "nitro" means an —$NO_2$ radical.

The term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl", alone or in combination, means a straight-chain or branched-chain hydrocarbon radical having one or more double bonds and containing from 2 to about 9 carbon atoms. The alkenyl radical may be attached through a double bond to a carbon atom in the fused ring. Examples of suitable alkenyl radicals include ethenyl, propenyl, allyl, 1,4-butadienyl and the like.

The term "alkynyl", alone or in combination, means a straight-chain or branched-chain hydrocarbon radical having one or more triple bonds and containing from 2 to about 18 carbon atoms preferably from 2 to about 8 carbon atoms. The alkynyl radical may be attached through a triple bond to a carbon atom. Examples of suitable alkynyl radicals include ethynyl, propynyl, and the like.

The term sulfonyl means a —$SO_2$— radical.

The term carbonyl means a —CO— radical.

The term amido means an —$NH_2$ radical with one of the H atoms substituted by a group having acidic character. Examples of suitable amido radicals include $CH_3CONH$— and the like.

The term "amino" means an —$NH_2$ with optionally one or more of the H atoms substituted by alkyl radicals as defined above. Examples of such "amino" radicals include —$NHCH_3$, —$N(CH_3)_2$ and the like.

The term "cycloalkyl" means a 3-, 4-, 5-, 6-, or 7-membered single aliphatic ring.

The term "cycloalkenyl" means a 4-, 5-, 6-, or 7-membered single aliphatic ring with a double bond present in the ring.

The term "aryl" alone or in combination, means a carbocyclic aromatic system containing one, two or three rings wherein such rings may be attached together in a pendent manner or may be fused. Examples of "aryl" include phenyl or naphthyl radicals either of which optionally carries one or more substituents selected from alkyl, alkoxy, halogen, hydroxy, amino, nitro and the like, as well as p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "heteroaryl", alone or in combination, means an aromatic system containing one, two or three rings, wherein such rings may be attached together in a pendent manner or may be fused, which include at least one and up to four heteroatoms, such as nitrogen, sulfur, and/or oxygen. Examples of "heteroaryl" include thienyl, furanyl, pyridinyl, imidazolyl, thiazolyl, pyrimidinyl, pyrazinyl, pyridazinyl, (is)oxazolyl, thiazolyl, tetrazolyl, pyrrolyl, pyridinyl-N-oxide, indolizinyl, indolyl, isoindolyl, indolinyl, benzofuranyl, benzothienyl, benzimidazolyl, purinyl, quinolinyl, isoquinolinyl and the like.

The term "heterocycle" means a non-aromatic system containing heteroatoms, such as oxygen, sulfur, nitrogen and the like. Examples of "heterocycle" include, morpholine, pyrolidine, piperidine, pyran and the like.

The term "alkoxy" embraces linear or branched oxy-containing radicals each having alkyl portions of one to ten carbon atoms, such as a methoxy radical.

The term "halo" means fluorine, chlorine, bromine or iodine.

The term "alkylcarbonyl" means a ketone radical containing a carbonyl CO radical attached to one carbon atom of an alkyl group as defined above. Examples of such "alkylcarbonyl" radical include —$COCH_3$, —$COCH_2CH_3$ and the like.

The term "arylcarbonyl" means a ketone radical containing a carbonyl CO radical attached to one carbon atom of an aryl radical as defined above. Examples of such "arylcarbonyl" radical include —$COC_6H_5$, —$COC_{10}H_7$ and the like.

The term "carboxyalkyl" means a carboxylic acid radical, C(=O)OH, attached to one carbon atom of an alkyl radical as defined above. Examples of such "carboxyalkyl" radical include —$CH_2CO_2H$, —$CH_2CH_2CO_2H$ and the like.

The term "alkoxycarbonyl" means an alkoxy radical attached to a carbonyl radical C=O. Examples of such "alkoxycarbonyl" radicals include —$CO_2CH_3$, —$CO_2CH_2CH_3$ and the like.

The invention relates to compounds having a structure of Formula I,

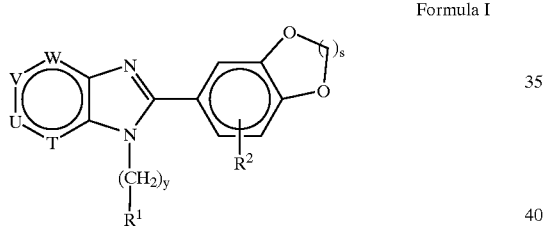

Formula I or a pharmaceutically acceptable salt thereof;
wherein y is an integer from 0 to 6;
wherein s is an integer from 1 to 3;
wherein $R^1$ is selected from the group consisting of hydrido, alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl, heterocycle, bicyclic aryl, heteroaryl and aryl, and wherein alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl, and heterocycle may be optionally substituted by one or more substituent(s) independently selected from the group consisting of alkyl, alkyl sulfonyl, alkenyl, alkynyl, amino, hydroxy and alkoxy, and wherein bicyclic aryl, heteroaryl and aryl may be optionally substituted by one or more substituent(s) independently selected from the group consisting of halo, nitro, alkyl, alkyl sulfonyl, alkenyl, alkynyl, amino, hydroxy, alkoxy, alkoxycarbonyl, and —O—$(CH_2)_p$—O—, wherein p is an integer from 1 to 3 and the oxygen atoms are bonded to adjacent carbons; wherein $R^2$ is selected from the group consisting of hydrido, hydroxy, halo, nitro, alkyl, alkyl sulfonyl, alkoxy, alkenyl, alkynyl and amino; and wherein T, U, V, and W are each independently N or $CR^3$ with the proviso that at least one of T, U, V, and W is $CR^3$, wherein each $R^3$ when present is independently selected from the group consisting of hydrido, hydroxy, halo, nitro, alkyl, alkyl sulfonyl, alkoxy, alkenyl, alkynyl and amino, and with the proviso that Formula I is not Benzimidazole-2-(3,4-methylenedioxyphenyl)-5-methyl, Benzimidazole-1-piperonyl-2-(3,4-methylene dioxyphenyl)-5-chloro, Benzimidazole-1-piperonyl-2-(3,4-methylenedioxyphenyl)-6-nitro, Benzimidazole-1-piperonyl-2-(3,4-methylenedioxyphenyl)-6-methyl, Benzimidazole-1-piperonyl-2-(3,4-methylenedioxyphenyl), Benzimidazole-2-(3,4-methylenedioxyphenyl)-5-nitro, Benzimidazole-2-(3,4-methylenedioxyphenyl)-6-nitro, Benzimidazole-2-(3,4-methylenedioxyphenyl)-5-chloro, Benzimidazole-2-(3,4-methylenedioxyphenyl)-6-chloro, 1H-Purine-8-(2,3-dihydro-1,4-benzodioxin-6-yl), 1H-Imidazol-[4,5-c]pyridine-2-(2,3-dihydro-1,4-benzo dioxin-6-yl), 1H-Purine-8-(2,3-dihydro-1,4-benzodioxin-6-yl)-monohydrochloride, 1H-Imidazol[4,5-c]pyridine-2-(2,3-dihydro-1,4-benzodioxin-6-yl)-monohydrochloride, Benzimidazole-1-benzyl-2-(3,4-methylenedioxyphenyl), Benzimidazole-1-benzyl-2-(3,4-methylenedioxyphenyl)-5-nitro, Benzimidazole-1-methyl-2-(3,4-methylene dioxyphenyl)-6-chloro, Benzimidazole-1,6-dimethyl-2-(3,4-methylenedioxyphenyl), Benzimidazole-2-(3,4-methylenedioxyphenyl)-4-methyl, Benzimidazole-1-(3,4-methylenedioxyphenyl)-2-(3,4-methylenedioxyphenyl)-4-methyl, Benzimidazole-1-benzyl-2-(3,4-methylenedioxy phenyl)-6-chloro, Benzimidazole-1-benzyl-2-(3,4-methylenedioxyphenyl)-5-methyl, Benzimidazole-1-benzyl-2-(3,4-methylenedioxyphenyl)-6-methyl, Benzimidazole-1-benzyl-2-(3,4-methylenedioxyphenyl)-5-chloro, Benz imidazole-1,5-dimethyl-2-(3,4-methylenedioxyphenyl), Benzimidazole-1-methyl-2-(3,4-methylenedioxyphenyl), Benzimidazole-2-(3,4-methylenedioxyphenyl), Benzimidazole-1-methyl-2-(3,4-methylenedioxyphenyl)-5-methyl, Benzimidazole-1-(3,4-methylenedioxyphenyl methyl)-2-(3,4-methylenedioxyphenyl)-5-methyl, or Benzimidazole-1-(3,4-methylenedioxyphenylmethyl)-2-(3,4-methylenedioxyphenyl)-5-chloro.

The invention also relates to compounds having a structure of Formula II,

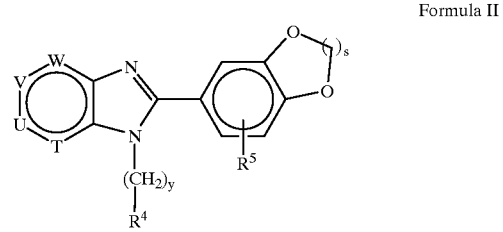

Formula II or a pharmaceutically acceptable salt thereof;
wherein y is an integer from 0 to 6;
wherein s is an integer from 1 to 3;
wherein $R^4$ is selected from the group consisting of alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl, heterocycle, bicyclic aryl, heteroaryl and aryl, any of which may be optionally substituted by one or more substituent(s) independently selected from the group consisting of alkyl, alkyl sulfonyl, alkenyl, alkynyl, amino, hydroxy and alkoxy, with the exception that alkenyl is not amino substituted and wherein bicyclic aryl, aryl and heteroaryl may also be optionally substituted by one or more substituent(s) independently selected from the group consisting of halo, nitro, alkoxycarbonyl and —O—$(CH_2)_p$—O—, wherein p is an integer from 1 to 3 and the oxygen atoms are bonded to adjacent carbons and with the proviso that $(CH_2)_y R^4$ is not methyl and with the proviso that when $R^4$ is substituted alkyl, the substituent is not amino;

wherein $R^5$ is selected from the group consisting of hydrido, hydroxy, halo, nitro, alkyl, alkyl sulfonyl, alkoxy, alkenyl, alkynyl and amino; and wherein T, U, V, and W are each independently N or $CR^6$ with the proviso that at least one of T, U, V, and W is $CR^6$, with the proviso that when T is N and U, V, and W is $CR^6$, $(CH_2)_y R^4$ is not $C_1–C_4$ alkyl, with the proviso that when T is N and U, V, and W are $CR^6$, $(CH_2)_y R^4$ is not benzyl, with the proviso that when W is N and T, U, and V are $CR^6$, $(CH_2)_y R^4$ is not benzyl and with the proviso that when T, U, V and W are all $CR^6$ and S is 1, then $(CH_2)_y R^4$ is not benzyl or 1,3-benzodioxolyl methyl group, wherein each $R^6$ when present is independently selected from the group consisting of hydrido, hydroxy, halo, nitro, alkyl, alkyl sulfonyl, alkoxy, alkenyl, alkynyl and amino and with the proviso that Formula II is not 2-(1,3-benzodioxol-5-yl)-1-(3,7-dimethyl-6-octen-1-yl)-1H-benzimidazole.

A more preferred class of compounds consists of those compounds of Formula II, wherein y is an integer from 1 to 3;

wherein $R^4$ is selected from the group consisting of alkyl, alkoxyalkyl, alkenyl, alkynyl, cycloalkyl, heterocycle, heteroaryl and aryl, any of which may be optionally substituted by one or more substituent(s) selected from the group consisting of alkyl, alkenyl, alkynyl, and alkoxy, and wherein heteroaryl and aryl may also be optionally substituted by one or more substituent(s) selected from the group consisting of halo, nitro, alkyl sulfonyl, alkoxycarbonyl, and —O—$(CH_2)_p$—O—, wherein p is an integer from 1 to 3 and the oxygen atoms are bonded to adjacent carbons;

wherein $R^5$ is selected from the group consisting of hydrido, hydroxy, halo, alkyl, and alkoxy; and wherein T, U, V, and W are each independently N or $CR^6$ with the proviso that at least one of T, U, V, and W is $CR^6$, wherein each $R^6$ when present is independently selected from the group consisting of hydrido, hydroxy, halo, nitro, alkyl, alkoxy, and amino.

An even more preferred class of compounds consists of those compounds of Formula II, wherein s is an integer from 1 to 2;

wherein $R^4$ is selected from the group consisting of alkyl, alkoxyalkyl, alkenyl, alkynyl, heteroaryl and aryl, any of which may be optionally substituted by one or more substituent(s) selected from the group consisting of alkyl and alkoxy, and wherein aryl or heteroaryl may also be optionally substituted by one or more substituent(s) selected from the group consisting of halo, nitro, alkenyl, alkoxycarbonyl, and —O—$(CH_2)_p$—O—, wherein p is an integer from 1 to 2 and the oxygen atoms are bonded to adjacent carbons; and wherein $R^5$ is selected from the group consisting of hydrido, hydroxy, halo, and alkoxy.

Most preferred compounds of Formula II, have one of the following structures:

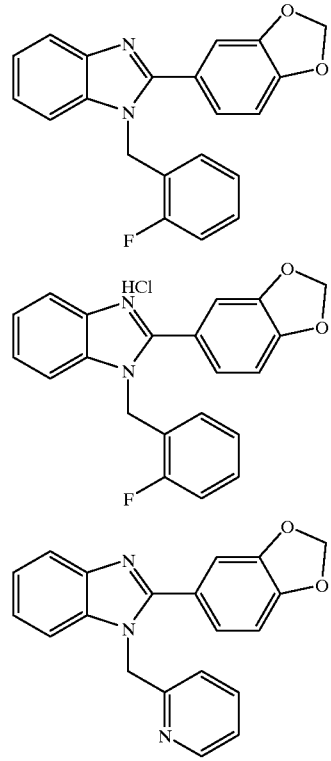

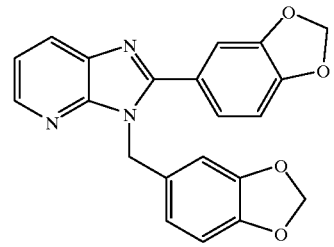

and

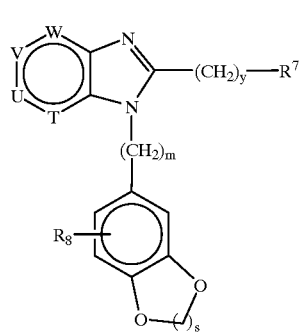

The invention also relates to compounds having a structure of Formula III,

Formula III or a pharmaceutically acceptable salt thereof;

wherein m is an interger from 0 to 3;

wherein y is an integer from 0 to 6;

wherein s is an integer from 1 to 3;

wherein R⁷ is selected from the group consisting of alkyl, alkoxyalkyl, carboxyalkyl, alkylcarbonyl, arylcarbonyl, alkenyl, alkoxyalkenyl, alkynyl, alkoxyalkynyl, cycloalkyl, cydloalkenyl, heterocycle, bicyclic aryl, heteroaryl and aryl, any of which may be optionally substituted by one or more substituent(s) selected from the group consisting of alkyl, alkyl sulfonyl, alkenyl, alkynyl, amino, hydroxy and alkoxy, and wherein bicyclic aryl, aryl and heteroaryl may also be optionally substituted by one or more substituent(s) selected from the group consisting of halo, nitro, alkoxycarbonyl, and —O—(CH₂)$_p$—O—, wherein p is an integer from 1 to 3 and the oxygen atoms are bonded to adjacent carbons, with the proviso that when m is 1, s is 1, and T, U, V and W are CR⁹, then (CH₂)$_y$R⁷ is not methyl, ethyl or 1,3-benzodioxolyl group;

wherein R⁸ is selected from the group consisting of hydrido, hydroxy, halo, nitro, alkyl, alkyl sulfonyl, alkoxy, alkenyl, alkynyl and amino; and wherein T, U, V, and W are each independently N or CR⁹ and with the proviso that at least one of T, U, V, and W is CR⁹, wherein each R⁹ when present is independently selected from the group consisting of hydrido, hydroxy, nitro, alkyl, alkyl sulfonyl, alkoxy, alkenyl, alkynyl and amino and with the proviso that when T is N, M is 0 and S is 1, then (CH₂)$_y$R⁷ is not phenyl.

A more preferred class of compounds consists of those compounds of Formula III, wherein m is an integer from 1 to 3;

wherein s is an integer from 1 to 3;

wherein R⁷ is selected from the group consisting of alkyl, alkoxyalkyl, alkenyl, alkynyl, cycloalkyl, heterocycle, heteroaryl and aryl, any of which may be optionally substituted by one or more substituent(s) selected from the group consisting of alkyl, alkenyl, alkynyl, and alkoxy, and wherein heteroaryl and aryl may also be optionally substituted by one or more substituent(s) selected from the group consisting of halo, nitro, alkyl sulfonyl, alkoxycarbonyl, and —O—(CH₂)$_p$—O—, wherein p is an integer from 1 to 3 and the oxygen atoms are bonded to adjacent carbons;

wherein R⁸ is selected from the group consisting of hydrido, hydroxy, halo, alkyl, and alkoxy; and wherein T, U, V, and W are each independently N or CR⁹ and with the proviso that at least one of T, U, V, and W is CR⁹, wherein R⁹ is selected from the group consisting of hydrido, hydroxy, nitro, alkyl, alkoxy, and amino.

An even more preferred class of compounds consists of those compounds of Formula III, wherein s is an integer from 1 to 2;

wherein R⁷ is selected from the group consisting of alkyl, alkoxyalkyl, alkenyl, alkynyl, heteroaryl and aryl, any of which may be optionally substituted by one or more substituent(s) selected from the group consisting of alkyl and alkoxy, and wherein heteroaryl and aryl may also be optionally substituted by one or more substituent(s) selected from the group consisting of halo, nitro, alkenyl, alkoxycarbonyl, and —O—(CH₂)$_p$—O—, wherein p is an integer from 1 to 2 and the oxygen atoms are bonded to adjacent carbons; and wherein R⁸ is selected from the group consisting of hydrido, hydroxy, halo, and alkoxy.

The present invention further provides for a pharmaceutical composition comprising a therapeutically effective amount of any of the compounds of the present invention. A "therapeutically effective amount" is any amount of a compound which, when administered to a subject suffering from a disease against which the compounds are effective, causes reduction, remission, or regression of the disease.

The invention provides for a method of treating glaucoma, impotence, asthma and cardiovascular disorders such as stable-, unstable- and variant-angina, hypertension, pulmonary hypertension, congestive heart failure, atherosclerosis, and thrombosis, which comprises administering a therapeutically effective amount of a compound of Formula II,

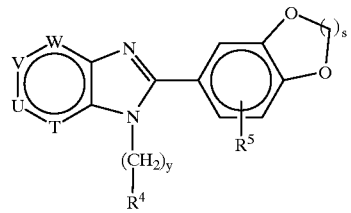

Formula II or a pharmaceutically acceptable salt thereof;

wherein y is an integer from 0 to 6;

wherein s is an integer from 1 to 3;

wherein R⁴ is selected from the group consisting of alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl, heterocycle, bicyclic aryl, heteroaryl and aryl, any of which may be optionally substituted by one or more substituent(s) independently selected from the group consisting of alkyl, alkyl sulfonyl, alkenyl, alkynyl, amino, hydroxy and alkoxy, and wherein bicyclic aryl, aryl and heteroaryl may also be optionally substituted by one or more substituent(s) independently selected from the group consisting of halo, nitro, alkoxycarbonyl and —O—(CH₂)$_p$—O—, wherein p is an integer from 1 to 3 and the oxygen atoms are bonded to adjacent carbons;

wherein R⁵ is selected from the group consisting of hydrido, hydroxy, halo, nitro, alkyl, alkyl sulfonyl, alkoxy, alkenyl, alkynyl and amino; and wherein T, U, V, and W are each independently N or CR⁶ with the proviso that at least one of T, U, V, and W is CR⁶, wherein each R⁶ when present is independently selected from the group consisting of hydrido, hydroxy, halo, nitro, alkyl, alkyl sulfonyl, alkoxy, alkenyl, alkynyl and amino.

Particularly preferred embodiments of the compounds of Formula II for use in the method of treatment of the diseases listed herein include the following:

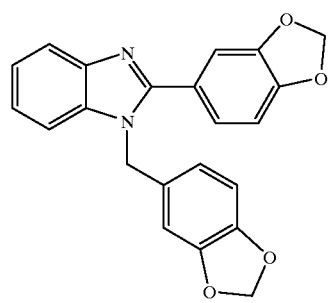

-continued
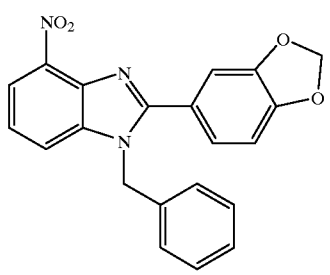
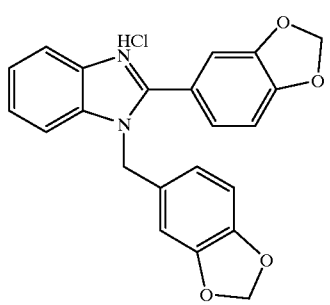
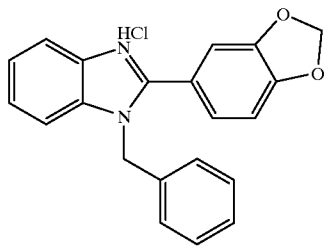
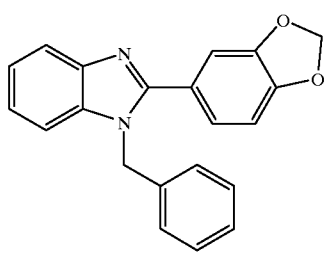
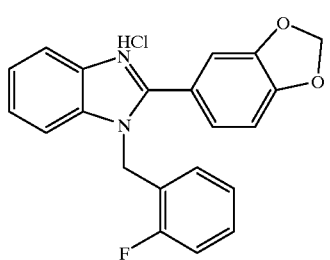
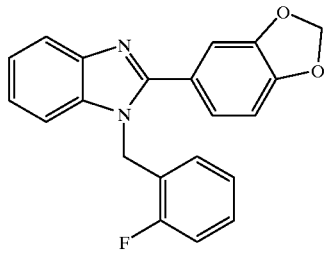
-continued
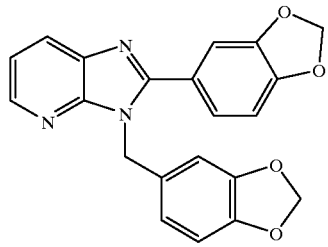
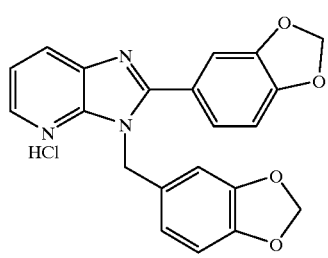
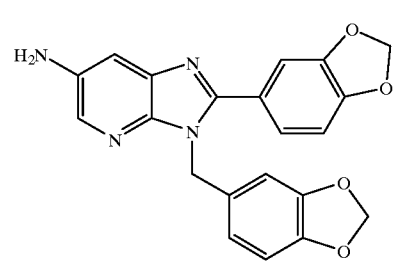
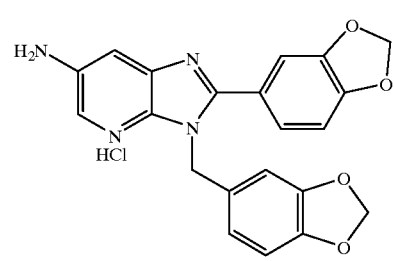
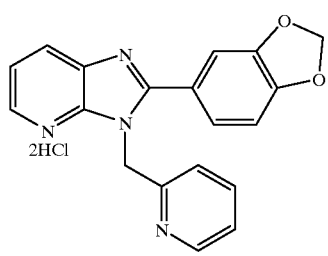
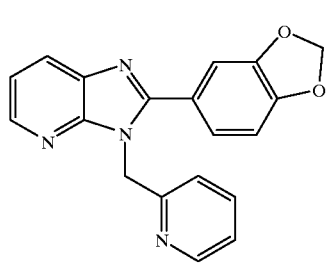
and -continued

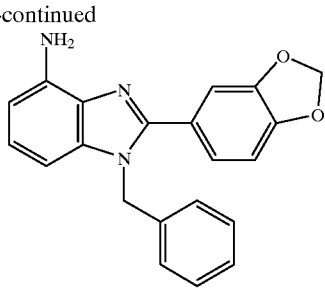

The present invention further provides a method of treating glaucoma, impotence, asthma and cardiovascular disorders such as stable-, unstable- and variant-angina, hypertension, pulmonary hypertension, congestive heart failure, atherosclerosis, and thrombosis, which comprises administering a therapeutically effective amount of a compound of Formula III,

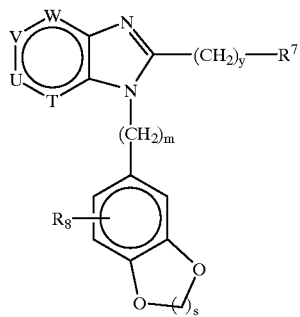

Formula III or a pharmaceutically acceptable salt thereof;
  wherein m is an integer from 0 to 3;
  wherein y is an integer from 0 to 6;
  wherein s is an integer from 1 to 3;
  wherein $R^7$ is selected from the group consisting of alkyl, alkoxyalkyl, carboxyalkyl, alkylcarbonyl, arylcarbonyl, alkenyl, alkoxyalkenyl, alkynyl, alkoxyalkynyl, cycloalkyl, cycloalkenyl, heterocycle, bicyclic aryl, heteroaryl and aryl, any of which may be optionally substituted by one or more substituent(s) selected from the group consisting of alkyl, alkyl sulfonyl, alkenyl, alkynyl, amino, hydroxy and alkoxy, and wherein bicyclic aryl, aryl and heteroaryl may also be optionally substituted by one or more substituent(s) selected from the group consisting of halo, nitro, alkoxycarbonyl, and —O—$(CH_2)_p$—O—, wherein p is an integer from 1 to 3 and the oxygen atoms are bonded to adjacent carbons;
  wherein $R^8$ is selected from the group consisting of hydrido, hydroxy, halo, nitro, alkyl, alkyl sulfonyl, alkoxy, alkenyl, alkynyl and amino; and
  wherein T, U, V, and W are each independently N or $CR^9$ and with the proviso that at least one of T, U, V, and W is $CR^9$, wherein each $R^9$ when present is independently selected from the group consisting of hydrido, hydroxy, nitro, alkyl, alkyl sulfonyl, alkoxy, alkenyl, alkynyl and amino.

Also included in the family of compounds of Formulae I–III are isomeric forms including diastereoisomers, regioisomers, tautomers and the pharmaceutically-acceptable salts thereof. The term "pharmaceutically-acceptable salts" embraces salts commonly used to form alkali metal salts and to form addition salts of free acids or free bases. The salts include but are not limited to the following acids and bases. The following inorganic acids; hydrochloric acid, hydrofluoric acid, hydrobromic acid, hydroiodic acid, sulfuric acid, nitric, carbonic, sulfuric, phosphoric acid and boric acid.

Appropriate organic acids may be selected from aliphatic, cycloaliphatic, aromatic, araliphatic, heterocyclic, carbonyllic and sulfonic classes of organic acids, example of which are formic, acetic, trifluoroacetic, malic, propionic, oxalic, malonic, succinic, glycolic, gluconic, lactic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, trifluoromethane sulfonic, ethanesulfonic, 2-hydroxyethanesulfonic, pantothenic, benzenesulfonic, toluenesulfonic, sulfanilic, mesylic, cyclohexylaminosulfonic, stearic, algenic, b-hydroxybutyric, malonic, galactaric, galacturonic, benzoic acid, glycolic acid, lactic acid and mandelic acid. The following inorganic bases; ammonia, hydroxyethylamine and hydrazine. The following organic bases; methylamine, ethylamine, propylamine, dimethylamine, diethylamine, trimethylamine, triethylamine, ethylenediamine, hydroxyethylamine, morpholine, piperazine and guanidine.

Suitable pharmaceutically-acceptable base addition salts of compounds of Formulae I–III include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylgluca-mine) and procaine. All of these salts may be prepared by conventional means from the corresponding compound of Formulae I–III by reacting, for example, the appropriate acid or base with the compound of Formulae I–III. This invention further provides for the hydrates and polymorphs of all of the compounds described herein.

General Synthetic Procedures

General synthetic methods for preparing the compounds of the present invention are illustrated in the Schemes 2 and 3. It is understood by those familiar with the art of organic synthesis that some functionality present in certain compounds of the invention may be incompatible with a particular synthetic sequence. Depending on the reactions and techniques employed, an alternative route, an altered order of steps, or a strategy of protection and deprotection may be necessary to prepare those compounds. In all cases, to achieve optimal yields the reaction conditions (such as reagents, solvent, temperature, and time) may need some modification. The benzimidazole-based, pyridine imidazole-based, pyrazineimidiazole-based, pyrimidine imidazole-based, pyridazineimidazole-based, and triazineimidazole-based cyclic GMP phosphodiesterase inhibitors may be prepared as shown in Schemes 2 and 3.

The following abbreviations are used in the schemes and experimental procedures: acetic acid ("HOAc"), sodium acetate ("NaOAc"), triethylamine ("TEA"), trifluoro acetic acid ("TFA"), lithium diisopropylamide ("LDA"), potassium tert-butoxide ("KOt-Bu"), 1,2-dimethoxyethane ("DME"), N,N-dimethylformamide ("DMF"), dimethyl sulfoxide ("DMSO"), isopropanol ("IPA"), ethyl acetate ("EtOAc"), tetrahydrofuran ("THF"), fast atom bombardment mass spectroscopy ("HRMS"), normal-("n-"), phenyl ("Ph"), room temperature ("rt"), secondary-("sec-"), tertiary ("tert-"), tosylate ("TsO"), triphenylmethyl ("Trityl"), and calculation ("Calc'd").

Synthetic Scheme 2 shows the method used to prepare Formulae I and II type bicyclic arylimidazoles or heteroarylimidazole derivatives. In step one, a nitrobenzene solution of an appropriate substituted benzaldehyde or benzoic acid is stirred with aryl or heteroaryl diamine 1 under reflux until the reaction is complete to give the bicyclic imidazole intermediate 2. In step 2, the bicyclic imidazole intermediate 2 in DMF at 0° C. is treated with potassium tert-butoxide, followed by the addition of an alkylating agent ($R^1(CH_2)_y$-halide) to give the final N-alkylated bicyclic imidazole 3 product.

Synthetic Scheme 3 shows the method used to prepare Formula III type bicyclic arylimidazoles or heteroarylimidazole derivatives. In step one, a nitrobenzene solution of an appropriate substituted aldehyde or carboxylic acid is stirred with aryl or heteroaryl diamine 4 under reflux until the reaction is complete to give the bicyclic imidazole intermediate 5. In step 2, the bicyclic imidazole intermediate 5 in DMF at 0° C. is treated with potassium tert-butoxide, followed by the addition of an alkylating agent (arylalkyl-halide) to give the final N-alkylated bicyclic imidazole 6 product.

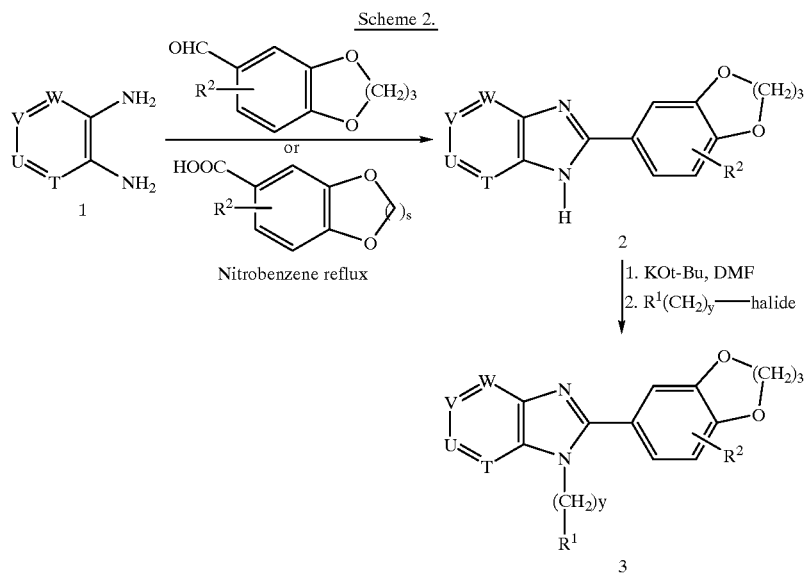

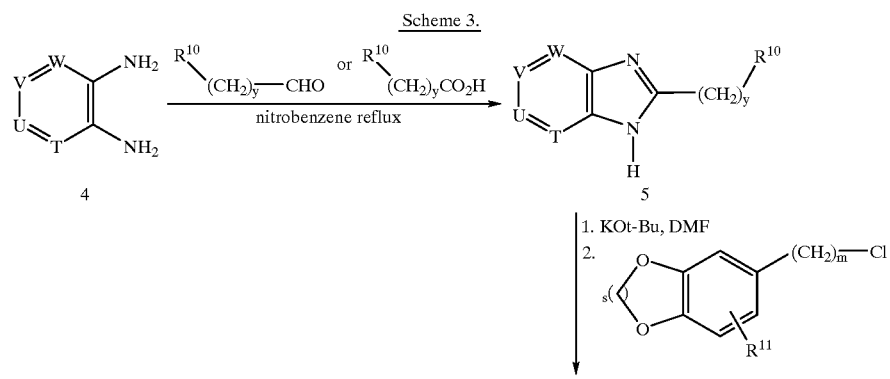

-continued

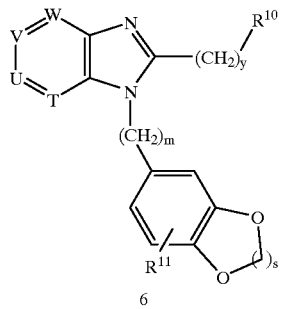

The Examples which follow are intended as illustrations of certain preferred embodiments of the invention, and no limitation of the invention is implied.

EXAMPLE 1

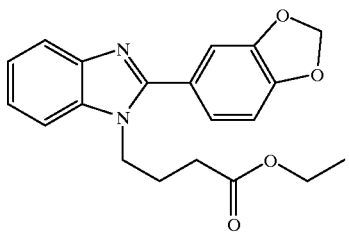

Ethyl 2-(1,3-benzodioxol-5-yl)-1H-benzimidazole-1-butanoate

Step 1: Preparation of 2-(1,3-benzodioxol-5-yl)-1H-benzimidazole

A solution of 50 g (0.34 mol) of piperonal and 37 g (0.34 mol) of phenylenediamine in 0.3 L of nitrobenzene was stirred under reflux for 12 hours. The resulting mixture was concentrated in vacuo. The solid residue was collected via filtration, and rinsed with ether to give 39.6 g (49%) of desired material as an off-white solid: $^1$H NMR (CDCl$_3$) δ 5.96 (s, 2H), 6.79 (d, J=8.5 Hz, 1H), 7.17–7.30 (m, 2H), 7.50–7.65 (m, 4H), 8.80–9.40 (br s, 1H).

Step 2: Preparation of ethyl 2-(1,3-benzodioxol-5-yl)-1H-benzimidazole-1-butanoate A solution of 10 g (42 mmol) of benzimidazole in 100 mL of DMF (N,N-dimethylformamide) at 0° C. was added 57 mL (57 mmol) of potassium tert-butoxide (1 M in THF), and the resulting dark solution was stirred at 0° C. for 10 min, then at rt for 15 min. To the resulting solution was added 11.2 mL (70 mmol) of ethyl 5-bromovalerate and the reaction was stirred at rt until completion. The mixture was concentrated in vacuo to half of original volume, and diluted with 200 mL of water and 200 mL of ether. The aqueous layer was extracted with another three 150 mL portions of ether. The combined extracts were washed with 100 mL of water and 100 mL of brine, dried (MgSO$_4$), and concentrated in vacuo. The residue was purified by silica gel chromatography to give 11 g (74%) of ethyl 2-(1,3-benzodioxol-5-yl)-1H-benzimidazole-1-butanoate as an oil: $^1$H NMR (CDCl$_3$) δ 1.22 (t, J=7.3 Hz, 3H), 2.11 (quintet, J=6.9 Hz, 2H), 2.25 (t, J=7.7 Hz, 2H), 4.07 (q, J=6.9 Hz, 2H), 4.31 (t, J=7.7 Hz, 2H), 6.05 (s, 2H), 6.94 (d, J=8.5 Hz, 1H), 7.15–7.24 (m, 2H), 7.27–7.35 (m, 2H), 7.40–7.50 (m, 1H), 7.76–7.85 (m, 1H); HRMS (EI) Calc'd for M$^+$: 352.1423, found: 352.1455.

EXAMPLE 2

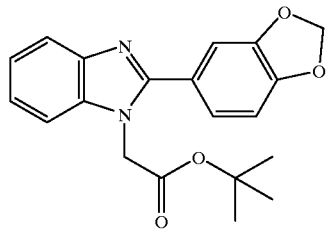

1,1-Dimethylethyl 2-(1,3-benzodioxol-5-yl)-1H-benzimidazole-1-acetate

Following a procedure similar to the one described in EXAMPLE 1, with the substitution of 1,1-dimethylethyl bromoacetate for ethyl 5-bromovalerate (Step 2, EXAMPLE 1), 1,1-dimethylethyl 2-(1,3-benzodioxol-5-yl)-1H-benzimidazole-1-acetate was prepared from 2-(1,3-benzodioxol-5-yl)-1H-benzimidazole (Step 1, EXAMPLE 1) as an oil: $^1$H NMR (CDCl$_3$) δ 1.45 (s, 9H), 4.78 (s, 2H), 6.05 (s, 2H), 6.93 (d, J=8.5 Hz, 1H), 7.18–7.23 (m, 2H), 7.25–7.37 (m, 3H), 7.77–7.85 (m, 1H); HRMS (EI) Calc'd for M$^+$: 352.1423, found: 352.1455. Anal. Calc'd for C$_{20}$H$_{20}$N$_2$O$_4$: C, 68.17; H, 5.72; N, 7.95. Found: C, 68.35; H, 5.93; N, 7.91.

EXAMPLE 3

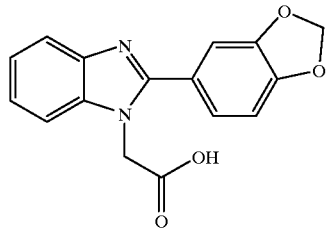

2-(1,3-Benzodioxol-5-yl)-1H-benzimidazole-1-acetic acid

A solution of 0.5 g (1.42 mmol) of 1,1-dimethylethyl 2-(1,3-benzodioxol-5-yl)-1H-benzimidazole-1-acetate (the title compound of EXAMPLE 2) in 10 mL of chloroform was treated with 10 mL of trifluoro-acetic acid (TFA), and the reaction was stirred at rt until completion. Volatiles were evaporated in vacuo, and the residue was recrystallized from ether to give 2-(1,3-benzodioxol-5-yl)-1H-benzimidazole-1-acetic acid as a white solid: $^1$H NMR (DMSO, d$_6$) δ 5.25 (s, 2H), 6.18 (s, 2H), 7.19 (d, J=8.1 Hz, 1H), 7.23–7.35 (m, 2H), 7.37–7.53 (m, 2H), 7.70–7.87 (m, 2H); HRMS (EI) Calc'd for M+: 297.0875, found: 297.0885. Anal. Calc'd for [$C_{16}H_{12}N_2O_4$+0.67 $CF_3CO_2H$]: C, 55.91; H, 3.43; N, 7.52. Found: C, 55.91; H, 3.52; N, 7.51.

EXAMPLE 4

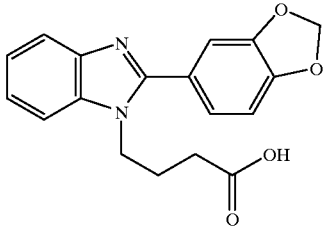

2-(1,3-Benzodioxol-5-yl)-1H-benzimidazole-1-butanoic acid

A solution of 4 g (11.4 mmol) of ethyl 2-(1,3-benzodioxol-5-yl)-1H-benzimidazole-1-butanoate in 40 mL of THF was treated with 40 mL (80 mmol) of lithium hydroxide (2M in water), and the reaction was stirred at rt overnight. The mixture was washed with ether to remove non-acidic impurity. The aqueous layer was acidified with 3 N hydrochloric acid (HCl), and the solid was collected by filtration and dried in vacuo to give 2.77 g (75%) of 2-(1,3-benzodioxol-5-yl)-1H-benzimidazole-1-butanoic acid as an off-white solid: mp 177.0–179.8° C.; $^1$H NMR (DMSO, $d_6$) δ 1.90 (quintet, J=7.3 Hz, 2H), 2.19 (t, J=6.9 Hz, 2H), 4.30 (t, J=7.7 Hz, 2H), 6.14 (s, 2H), 7.10 (d, J=8.1 Hz, 1H), 7.20–7.34 (m, 4H), 7.65 (dd, J=7.9, 1.2 Hz, 2H), 12.15 (br s, 1H); HRMS (EI) Calc'd for M+: 325.1188, found: 325.1188. Anal. Calc'd for [$C_{18}H_{16}N_2O_4$+0.43 $CH_2Cl_2$]: C, 61.39; H, 4.71; N, 7.77. Found: C, 61.39; H, 4.55; N, 7.79.

EXAMPLE 5

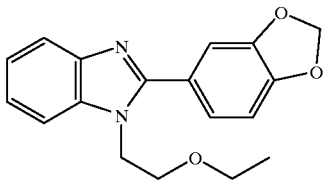

2-(1,3-Benzodioxol-5-yl)-1-(2-ethoxyethyl)-1H-benzimidazole

Following a procedure similar to the one described in EXAMPLE 1, with the substitution of 2-bromoethyl ethyl ether for ethyl 5-bromovalerate (Step 2, EXAMPLE 1), 2-(1,3-Benzodioxol-5-yl)-1-(2-ethoxyethyl)-1H-benzimidazole was prepared from 2-(1,3-benzodioxol-5-yl)-1H-benzimidazole (Step 1, EXAMPLE 1) as an oil: $^1$H NMR (CDCl$_3$) δ 1.13 (t, J=7.3 Hz, 3H), 3.41 (q, J=6.8 Hz, 2H), 3.82 (t, J=5.6 Hz, 2H), 4.40 (t, J=5.6 Hz, 2H), 6.05 (s, 2H), 6.94 (d, J=8.1 Hz, 1H), 7.30–7.40 (m, 4H), 7.40–7.50 (m, 1H), 7.75–7.85 (m, 1H); HRMS (EI) Calc'd for M+: 310.1317, found: 310.1347.

EXAMPLE 6

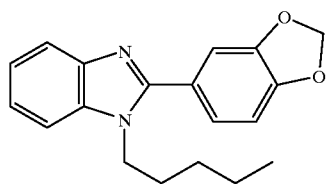

2-(1,3-Benzodioxol-5-yl)-1-pentyl-1H-benzimidazole

Following a procedure similar to the one described in EXAMPLE 1, with the substitution of iodopentane for ethyl 5-bromovalerate (Step 2, EXAMPLE 1), 2-(1,3-Benzodioxol-5-yl)-1-pentyl-1H-benzimidazole was prepared from 2-(1,3-Benzodioxol-5-yl)-1-(2-ethoxyethyl)-1H-benzimidazole (Step 1, EXAMPLE 1) as an oil: $^1$H NMR (CDCl$_3$) δ 0.85 (t, J=6.9 Hz, 3H), 1.17–1.38 (m, 4H), 1.81 (quintet, J=7.4 Hz, 2H), 4.21 (t, J=7.7 Hz, 2H), 6.06 (s, 2H), 6.94 (d, J=8.4 Hz, 1H), 7.17–7.22 (m, 2H), 7.25–7.33 (m, 2H), 7.35–7.43 (m, 1H), 7.75–7.85 (m, 1H); HRMS (EI) Calc'd for M+: 308.1525, found: 308.1536. Anal. Calc'd for $C_{19}H_{20}N_2O_2$: C, 74.00; H, 6.54; N, 9.08. Found: C, 73.94; H, 6.79; N, 9.10.

EXAMPLE 7

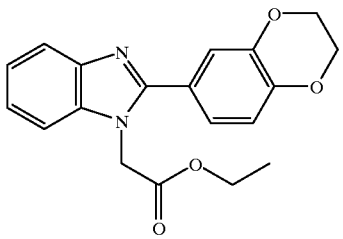

Ethyl 2-(2,3-dihydro-1,4-benzodioxin-6-yl)-1H-enzimidazole-1-acetate

Step 1: Preparation of 2-(2,3-dihydro-1,4-benzodioxin-6-yl)-1H-benzimidazole

Following a procedure similar to the one described in EXAMPLE 1 (Step 1), with the substitution of 1,4-benzodioxan-6-carboxaldehyde for piperonal, 2-(2,3-dihydro-1,4-benzodioxin-6-yl)-1H-benzimidazole was prepared as a solid: $^1$H NMR (DMSO, $d_6$) δ 4.32 (s, 4H), 7.02 (d, J=9.0 Hz, 1H), 7.10–7.25 (m, 2H), 7.48 (d, J=7.9 Hz, 1H), 7.55–7.73 (m, 3H), 12.70 (s, 1H); HRMS (EI) Calc'd for M+: 235.0977, found: 235.0973.

Step 2: Preparation of ethyl 2-(2,3-dihydro-1,4-benzodioxin-6-yl)-1H-benzimidazole-1-acetate Following a procedure similar to the one described in EXAMPLE 1 (Step 2), with the substitution of ethyl bromoacetate for ethyl 5-bromovalerate, ethyl 2-(2,3-dihydro-1,4-benzodioxin-6-yl)-1H-benzimidazole-1-acetate was prepared from 2-(2,3-dihydro-1,4-benzodioxin-6-yl)-1H-benzimidazole (from Step 1) as a solid: mp 112.8–113.5° C.; $^1$H NMR (CDCl$_3$) δ 1.28 (t, J=7.3 Hz, 3H), 4.20–4.40 (m, 6H), 4.92 (s, 2H), 7.00 (d, J=8.5 Hz, 1H), 7.20–7.40 (m, 5H), 7.80–7.95 (m, 1H); HRMS (EI) Calc'd for M+: 339.1345, found: 339.1375. Anal. Calc'd for $C_{19}H_{18}N_2O_4$: C, 67.45; H, 5.36; N, 8.28. Found: C, 66.94; H, 5.40; N, 8.21.

EXAMPLE 8

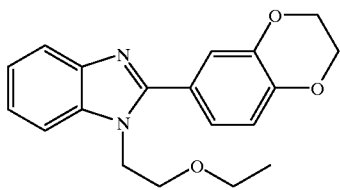

2-(2,3-Dihydro-1,4-benzodioxin-6-yl)-1-(2-ethoxyethyl)-H-benzimidazole

Following a procedure similar to the one described in EXAMPLE 1, with the substitution of 2-bromoethyl ethyl ether for ethyl 5-bromovalerate (Step 2, EXAMPLE 1), 2-(2,3-dihydro-1,4-benzodioxin-6-yl)-1-(2-ethoxyethyl)-1H-benzimidazole was prepared from 2-(2,3-dihydro-1,4-benzodioxin-6-yl)-1H-benzimidazole (Step 1, EXAMPLE 7) as a solid: $^1$H NMR (CDCl$_3$) δ 1.13 (t, J=7.0 Hz, 3H), 3.42 (q, J=7.0 Hz, 2H), 3.82 (t, J=5.8 Hz, 2H), 4.32 (s, 4H), 4.41 (t, J=5.8 Hz, 2H), 6.99 (d, J=8.4 Hz, 1H), 7.25–7.38 (m, 3H), 7.42 (d, J=2.1 Hz, 1H), 7.40–7.53 (m, 1H), 7.77–7.87 (m, 1H); HRMS (FAB) Calc'd for M+H: 325.1552, found: 325.1608.

EXAMPLE 9

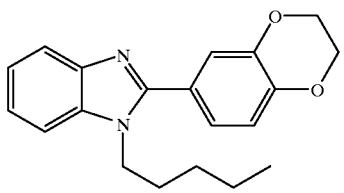

2-(2,3-Dihydro-1,4-benzodioxin-6-yl)-1-pentyl-1H-enzimidazole

Following a procedure similar to the one described in EXAMPLE 1, with the substitution of iodopentane for ethyl 5-bromovalerate (Step 2, EXAMPLE 1), 2-(2,3-dihydro-1,4-benzodioxin-6-yl)-1-pentyl-1H-benzimidazole was prepared from 2-(2,3-dihydro-1,4-benzodioxin-6-yl)-1H-benzimidazole (Step 1, EXAMPLE 7) as a solid: mp 82.2–82.7° C.; $^1$H NMR (CDCl$_3$) δ 0.86 (t, J=6.8 Hz, 3H), 1.20–1.40 (m, 4H), 1.82 (quintet, J=7.1 Hz, 2H), 4.21 (t, J=7.8 Hz, 2H), 4.27–4.40 (br s, 4H), 6.99 (d, J=8.3 Hz, 1H), 7.17–7.33 (m, 4H), 7.35–7.45 (m, 1H), 7.75–7.85 (m, 1H); HRMS (EI) Calc'd for M$^+$: 323.1760, found: 323.1766. Anal. Calc'd for C$_{20}$H$_{22}$N$_2$O$_2$: C, 74.51; H, 6.88; N, 8.69. Found: C, 74.35; H, 7.02; N, 8.56.

EXAMPLE 10

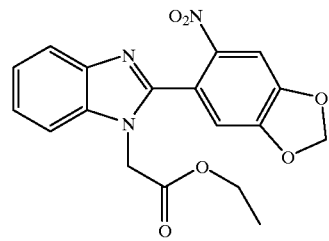

Ethyl 2-(6-nitro-1,3-benzodioxol-5-yl)-1H-benzimidazole-1-acetate

Step 1: Preparation of 2-(6-nitro-1,3-benzodioxol-5-yl)-1H-benzimidazole

Following a procedure similar to the one described in EXAMPLE 1 (Step 1), with the substitution of 6-nitropiperonal for piperonal, 2-(6-nitro-1,3-benzodioxol-5-yl)-1H-benzimidazole was prepared as a solid: $^1$H NMR (DMSO, d$_6$) δ 6.32 (s, 2H), 7.1–7.4 (m, 2H), 7.41 (s, 1H), 7.40–7.90 [m (with s at 7.72), 3H], 12.70–12.85 (br s, 1H).

Step 2: Preparation of ethyl 2-(6-nitro-1,3-benzodioxol-5-yl)-1H-benzimidazole-1-acetate Following a procedure similar to the one described in EXAMPLE 1 (Step 2), with the substitution of ethyl bromoacetate for ethyl 5-bromovalerate, ethyl 2-(6-nitro-1,3-benzodioxol-5-yl)-1H-benzimidazole-1-acetate was prepared from 2-(6-nitro-1,3-benzodioxol-5-yl)-1H-benzimidazole (from Step 1) as a solid: mp 136,5–138.0° C.; $^1$H NMR (CDCl$_3$) δ 1.24 (t, J=7.1 Hz, 3H), 4.20 (q, J=7.1 Hz, 2H), 4.72 (s, 2H), 6.23 (s, 2H), 7.04 (s, 1H), 7.30–7.45 (m, 3H), 7.72 (s, 1H), 7.75–7.90 (m, 1H); HRMS (FAB) Calc'd for M+H: 370.1039, found: 370.1101. Anal. Calc'd for C$_{18}$H$_{15}$N$_3$O$_6$+0.1 CH$_2$Cl$_2$: C, 57.58; H, 4.06; N, 11.13. Found: C, 57.54; H, 4.22; N, 11.25.

EXAMPLE 11

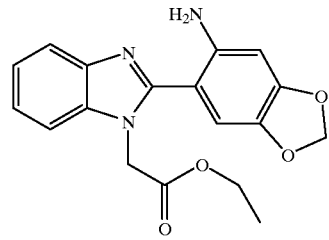

Ethyl 2-(6-amino-1,3-benzodioxol-5-yl)-1H-benzimidazole-1-acetate

A suspension of 1.0 g (2.71 mmol) of the ethyl 2-(6-nitro-1,3-benzodioxol-5-yl)-1H-benzimidazole-1-acetate from EXAMPLE 10 and 0.5 g of 10% palladium on carbon in 20 mL of absolute EtOH was agitated on a Parr apparatus under a hydrogen atmosphere at 32 psi for 3.5 h. The mixture was filtered through a pad of celite and concentrated to give the crude product mixture. Purification by silica gel chromatography gave 93 mg (9%) of ethyl 2-(6-amino-1,3-benzodioxol-5-yl)-1H-benzimidazole-1-acetate as a solid: mp 284.2–287° C.; $^1$H NMR (CDCl$_3$) δ 1.29 (t, J=7.2 Hz, 3H), 4.27 (q, J=7.1 Hz, 2H), 4.85 (s, 2H), 5.93 (s, 2H), 6.38 (s, 1H), 6.79 (s, 1H), 7.26–7.40 (m, 3H), 7.73–7.83 (m, 1H); HRMS (FAB) Calc'd for M+H: 340.1297, found: 340.1255.

EXAMPLE 12

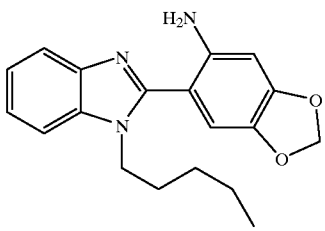

2-(6-Amino-1,3-benzodioxol-5-yl)-1-pentyl-1H-benzimidazole

Following a procedure similar to the one described in EXAMPLE 10 (Step 2), with the substitution of iodopentane for ethyl 5-bromovalerate, 2-(6-nitro-1,3-benzodioxol-5-yl)-1-pentyl-1H-benzimidazole was prepared from 2-(6-nitro-1,3-benzodioxol-5-yl)-1H-benzimidazole (from EXAMPLE 11, Step 1) as a solid which was used directly in the next step.

Following a procedure similar to the one described in EXAMPLE 11, 2-(6-amino-1,3-benzodioxol-5-yl)-1-pentyl-1H-benzimidazole was prepared from 2-(6-nitro-1,3-benzodioxol-5-yl)-1H-benzimidazole (obtained from above) as a white solid: mp 115.1–117.0° C.; $^1$H NMR (CDCl$_3$) δ 0.85 (t, J=6.9 Hz, 3H), 1.15–1.35 (m, 4H), 1.79 (quintet, J=7.3 Hz, 2H), 4.17 (t, J=7.7 Hz, 2H), 4.4–5.0 (br s, 2H), 5.94 (s, 2H), 6.39 (s, 1H), 6.74 (s, 1H), 7.26–7.35 (m, 2H), 7.35–7.44 (m, 1H), 7.72–7.83 (m, 1H); HRMS (FAB) Calc'd for M+H: 324.1712, found: 324.1752. Anal. Calc'd for [C$_{19}$H$_{21}$N$_3$O$_2$+0.06 CH$_2$Cl$_2$]: C, 69.74; H, 6.48; N, 12.80. Found: C, 69.71; H, 6.58; N, 12.88.

EXAMPLE 13

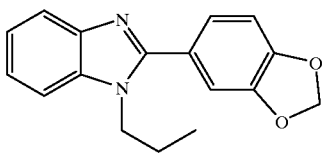

2-(1,3-Benzodioxol-5-yl)-1-propyl-1H-benzimidazole

Following a procedure similar to the one described in EXAMPLE 1, with the substitution of iodopropane for ethyl 5-bromovalerate (Step 2, EXAMPLE 1), 2-(1,3-benzodioxol-5-yl)-1-propyl-1H-benzimidazole was prepared from 2-(1,3-benzodioxol-5-yl)-1H-benzimidazole (Step 1, Example 1) as a solid: mp 77.5–78.0° C.; $^1$H NMR (CDCl$_3$) δ 0.88 (t, J=7.5 Hz, 3H), 1.84 (septet, J=7.5 Hz, 2H), 4.18 (t, J=7.7 Hz, 2H), 6.06 (s, 2H), 6.94 (d, J=8.4 Hz, 1H), 7.15–7.22 (m, 2H), 7.22–7.34 (m, 2H), 7.35–7.44 (m, 1H), 7.75–7.84 (m, 1H); HRMS (FAB) Calc'd for M+H: 281.1290, found: 281.1344. Anal. Calc'd for C$_{17}$H$_{16}$N$_2$O$_2$: C, 72.84; H, 5.75; N, 9.99. Found: C, 72.55; H, 5.49; N, 9.90.

EXAMPLE 14

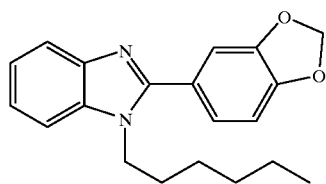

2-(1,3-Benzodioxol-5-yl)-1-hexyl-1H-benzimidazole

Following a procedure similar to the one described in Example 1, with the substitution of iodohexane for ethyl 5-bromovalerate (Step 2, Example 1), 2-(1,3-benzodioxol-5-yl)-1-hexyl-1H-benzimidazole was prepared from 2-(1,3-benzodioxol-5-yl)-1H-benzimidazole (Step 1, Example 1) as a solid: mp 60.5–61.6° C.; $^1$H NMR (CDCl$_3$) δ 0.84 (t, J=6.8 Hz, 3H), 1.15–1.35 (m, 6H), 1.80 (quintet, J=6.7 Hz, 2H), 4.21 (t, J=7.6 Hz, 2H), 6.06 (s, 2H), 6.94 (d, J=8.4 Hz, 1H), 7.13–7.22 (m, 2H), 7.22–7.34 (m, 2H), 7.35–7.43 (m, 1H), 7.75–7.85 (m, 1H); HRMS (EI) Calc'd for M+H: 323.1760, found: 323.1761. Anal. Calc'd for C$_{20}$H$_{22}$N$_2$O$_2$: C, 74.51; H, 6.88; N, 8.69. Found: C, 74.51; H, 6.87; N, 8.58.

EXAMPLE 15

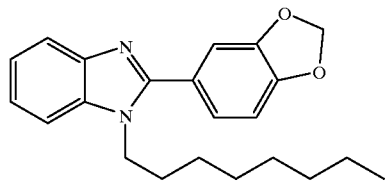

2-(1,3-Benzodioxol-5-yl)-1-octyl-1H-benzimidazole

Following a procedure similar to the one described in Example 1, with the substitution of iodooctane for ethyl 5-bromovalerate (Step 2, Example 1), 2-(1,3-benzodioxol-5-yl)-1-octyl-1H-benzimidazole was prepared from 2-(1,3-benzodioxol-5-yl)-1H-benzimidazole (Step 1, Example 1) as a solid: $^1$H NMR (CDCl$_3$) δ 0.87 (t, J=7.3 Hz, 3H), 1.13–1.38 (m, 10H), 1.80 (quintet, J=7.3 Hz, 2H), 4.21 (t, J=7.3 Hz, 2H), 6.06 (s, 2H), 6.95 (d, J=8.5 Hz, 1H), 7.12–7.22 (m, 2H), 7.22–7.35 (m, 2H), 7.35–7.43 (m, 1H), 7.75–7.85 (m, 1H); HRMS (FAB) Calc'd for M+H: 351.2073, found: 351.2075.

EXAMPLE 16

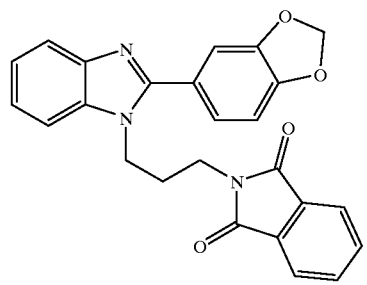

2-[3-[2-(1,3-Benzodioxol-5-yl)-1H-benzimidazol-5-yl]propyl]-2,3-dihydro-1H-isoindol-1,3-dione Following a procedure similar to the one described in Example 1, with the substitution of N-(3-bromopropyl)

phthalimide for ethyl 5-bromovalerate (Step 2, Example 1), 2-[3-[2-(1,3-benzodioxol-5-yl)-1H-benzimidazol-5-yl]propyl]-2,3-dihydro-1H-isoindol-1,3-dione was prepared from 2-(1,3-benzodioxol-5-yl)-1H-benzimidazole (Step 1, Example 1) as an oil: $^1$H NMR (CDCl$_3$) δ 2.23 (quintet, J=6.9 Hz, 2H), 3.74 (t, J=6.8 Hz, 2H), 4.31 (t, J=6.9 Hz, 2H), 5.98 (s, 2H), 6.78 (d, J=8.6 Hz, 1H), 7.10–7.20 [m (with s at 7.15), 2H], 7.25–7.45 (m, 3H), 7.70–7.78 (m, 2H), 7.78–7.90 (m, 3H); HRMS (EI) Calc'd for M$^+$: 426.1454, found: 426.1437.

EXAMPLE 17

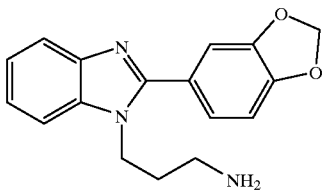

2-(1,3-Benzodioxol-5-yl)-1H-benzimidazole-1-propanamine

To a solution of 500 mg (1.18 mmol) of 2-[3-[2-(1,3-benzodioxol-5-yl)-1H-benzimidazol-5-yl]propyl]-2,3-dihydro-1H-isoindol-1,3-dione, the title compound of EXAMPLE 16, in 10 mL of ethanol was added 70 μL of hydrazine (2.3 mmol), and the resulting mixture was stirred at ambient temperature overnight. The mixture was concentrated in vacuo, and the residue was purified by silica gel chromatography to give 235 mg (68%) of 2-(1,3-benzodioxol-5-yl)-1H-benzimidazole-1-propanamine as an oil: $^1$H NMR (CDCl$_3$) δ 1.91 (quintet, J=7.0 Hz, 2H), 2.63 (t, J=7.0 Hz, 2H), 4.33 (t, J=7.2 Hz, 2H), 6.05 (s, 2H), 6.93 (d, J=8.7 Hz, 1H), 7.10–7.18 (m, 4H), 7.19–7.40 (m, 1H), 7.70–7.90 (m, 1H); HRMS (EI) Calc'd for M$^+$: 296.1399, found: 296.1438.

EXAMPLE 18

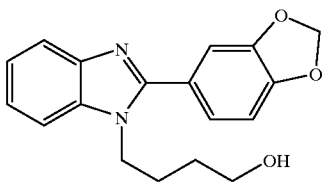

2-(1,3-Benzodioxol-5-yl)-1H-benzimidazole-1-butanol

To a solution of 762 mg (2.45 mmol) of ethyl 2-(1,3-benzodioxol-5-yl)-1H-benzimidazole-1-butanoate, the title compound of Example 1, in 12 mL of THF was added 2.45 mL of LAH (1M in THF) at ambient temperature, and the resulting mixture was stirred overnight. The reaction was quenched with water, extracted with ether, and the combined extracts were dried, and concentrated in vacuo. The residue was purified by silica gel chromatography to give 538 mg (83%) of 2-(1,3-benzodioxol-5-yl)-1H-benzimidazole-1-butanol as a colorless glass: $^1$H NMR (CDCl$_3$) δ 1.52 (quintet, J=7.8 Hz, 2H), 1.92 (quintet, J=7.7 Hz, 2H), 3.61 (t, J=6.2 Hz, 2H), 4.29 (t, J=7.7 Hz, 2H), 6.06 (s, 2H), 6.93 (d, J=8.4 Hz, 1H), 7.15–7.25 (m, 2H), 7.25–7.37 (m, 2H), 7.38–7.45 (m, 1H), 7.78–7.88 (m, 1H); HRMS (FAB) Calc'd for M+H: 311.1396, found: 311.1447. Anal. Calc'd for [C$_{18}$H$_{18}$N$_2$O$_3$+0.09 CH$_2$Cl$_2$]: C, 68.39; H, 5.77; N, 8.82. Found: C, 68.39; H, 5.81; N, 8.82.

EXAMPLE 19

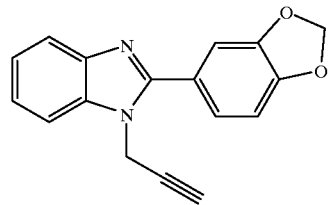

2-(1,3-Benzodioxol-5-yl)-1-(3-methyl-2-butenyl)-1H-benzimidazole

Following a procedure similar to the one described in Example 1, with the substitution of 4-bromo-2-methyl-2-butene for ethyl 5-bromovalerate (Step 2, Example 1), 2-(1,3-benzodioxol-5-yl)-1-(3-methyl-2-butenyl)-1H-benzimidazole was prepared from 2-(1,3-benzodioxol-5-yl)-1H-benzimidazole (Step 1, Example 1) as a white solid: mp 73.8–76.0° C.; $^1$H NMR (CDCl$_3$) δ 1.76 (s, 6H), 4.79 (d, J=6.0 Hz, 2H), 5.30–5.42 (m, 1H), 6.04 (s, 2H), 6.92 (d, J=8.6 Hz, 1H), 7.15–7.40 (m, 5H), 7.75–7.84 (m, 1H); HRMS (FAB) Calc'd for M+H: 307.1447, found: 307.1459. Anal. Calc'd for C$_{19}$H$_{18}$N$_2$O$_2$: C, 74.49; H, 5.92; N, 9.14. Found: C, 74.21; H, 5.61; N, 9.14.

EXAMPLE 20

2-(1,3-Benzodioxol-5-yl)-1-(2-propynyl)-1H-benzimidazole

Following a procedure similar to the one described in Example 1, with the substitution of propargyl chloride for ethyl 5-bromovalerate (Step 2, Example 1), 2-(1,3-benzodioxol-5-yl)-1-(2-propynyl)-1H-benzimidazole was prepared from 2-(1,3-benzodioxol-5-yl)-1H-benzimidazole (Step 1, Example 1) as a white solid: $^1$H NMR (CDCl$_3$) δ 5.64 (d, J=6.5 Hz, 2H), 6.08 (s, 2H), 6.97 (d, J=8.0 Hz, 1H), 7.14 (t, J=6.5 Hz, 2H), 7.28–7.42 (m, 4H), 7.75–7.85 (m, 2H); HRMS (FAB) Calc'd for M+H: 277.0977, found: 277.0966. Anal. Calc'd for [C$_{17}$H$_{12}$N$_2$O$_2$+0.06 CH$_2$Cl$_2$]: C, 72.87; H, 4.34; N, 9.96. Found: C, 72.90; H, 4.40; N, 9.77.

EXAMPLE 21

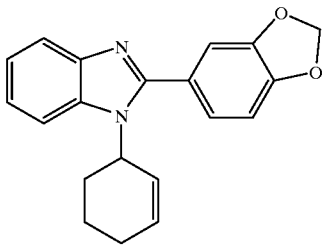

2-(1,3-Benzodioxol-5-yl)-1-(cyclohexen-3-yl)-1H-benzimidazole

Following a procedure similar to the one described in Example 1, with the substitution of 3-bromo-cyclohexene for ethyl 5-bromovalerate (Step 2, Example 1), 2-(1,3-benzodioxol-5-yl)-1-(cyclohexen-3-yl)-1H-benzimidazole was prepared from 2-(1,3-benzodioxol-5-yl)-1H-benzimidazole (Step 1, Example 1) as a white solid: mp 119.1–120.5° C.; $^1$H NMR (CDCl$_3$) δ 1.64–1.83 (m, 1H), 1.91–2.12 (m, 2H), 2.12–2.40 (m, 3H), 5.13–5.27 (m, 1H), 5.76 (d, J=7.7 Hz, 1H), 6.00–6.13 [m (with s at 6.07), 3H], 6.95 (d, J=8.5 Hz, 1H), 7.10–7.33 (m, 4H), 7.56 (d, J=7.2 Hz, 1H), 7.79 (d, J=7.3 Hz, 1H); HRMS (FAB) Calc'd for M+H: 319.1447, found: 319.1466. Anal. Calc'd for [C$_{20}$H$_{18}$N$_2$O$_2$+0.27 CH$_2$Cl$_2$]: C, 71.34; H, 5.48; N, 8.21. Found: C, 71.36; H, 5.30; N, 8.15.

EXAMPLE 22

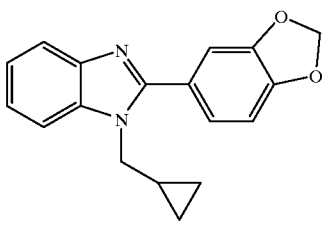

2-(1,3-Benzodioxol-5-yl)-1-cyclopropylmethyl-1H-benzimidazole

Following a procedure similar to the one described in Example 1, with the substitution of bromomethyl cyclopropane for ethyl 5-bromovalerate (Step 2, Example 1), 2-(1,3-benzodioxol-5-yl)-1-cyclopropylmethyl-1H-benzimidazole was prepared from 2-(1,3-benzodioxol-5-yl)-1H-benzimidazole (Step 1, Example 1) as an oil: $^1$H NMR (CDCl$_3$) δ 0.21(ABq, 2H), 0.52 (ABq, 2H), 1.10–1.30 (m, 1H), 4.15 (d, J=6.9 Hz, 2H), 6.07 (s, 2H), 6.95 (d, J=8.1 Hz, 1H), 7.16–7.25 (m, 2H), 7.28–7.30 (m, 2H), 7.42–7.51 (m, 1H), 7.77–7.90 (m, 1H); HRMS (FAB) Calc'd for M+H: 293.1290, found: 293.1259.

EXAMPLE 23

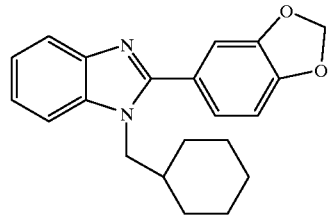

2-(1,3-Benzodioxol-5-yl)-1-cyclohexylmethyl-1H-benzimidazole

Following a procedure similar to the one described in Example 1, with the substitution of cyclohexylmethyl bromide for ethyl 5-bromovalerate (Step 2, Example 1), 2-(1,3-benzodioxol-5-yl)-1-cyclohexylmethyl-1H-benzimidazole was prepared from 2-(1,3-benzodioxol-5-yl)-1H-benzimidazole (Step 1, Example 1) as a white solid: mp 100.4–101.5° C.; $^1$H NMR (CDCl$_3$) δ 0.70–0.90 (m, 2H), 0.95–1.20 (m, 3H), 1.44 (br d, J=12.5 Hz, 2H), 1.50–1.70 (br m, 3H), 1.70–1.92 (m, 1H), 4.10 (d, J=7.3 Hz, 2H), 6.07 (s, 2H), 6.94 (d, J=8.5 Hz, 1H), 7.10–7.20 (m, 2H), 7.20–7.35 (m, 2H), 7.35–7.45 (m, 1H), 7.75–7.83 (m, 1H); HRMS (FAB) Calc'd for M+H: 335.1760, found: 335.1801. Anal. Calc'd for [C$_{21}$H$_{21}$N$_2$O$_2$+0.03 CH$_2$Cl$_2$]: C, 75.23; H, 6.32; N, 8.34. Found: C, 75.22; H, 6.60; N, 8.32.

EXAMPLE 24

2-(1,3-Benzodioxol-5-yl)-1-(2-cyclohexylethyl)-1H-benzimidazole

Following a procedure similar to the one described in Example 1, with the substitution of cyclohexylethyl bromide for ethyl 5-bromovalerate (Step 2, Example 1), 2-(1,3-benzodioxol-5-yl)-1-(2-cyclohexylethyl)-1H-benzimidazole was prepared from 2-(1,3-benzodioxol-5-yl)-1H-benzimidazole (Step 1, Example 1) as a white solid: mp 109.8–110.6° C.; $^1$H NMR (CDCl$_3$) δ 0.80–1.00 (m, 2H), 1.00–1.32 (m, 4H), 1.55–1.80 (m, 7H), 4.24 (t, J=7.7 Hz, 2H), 6.06 (s, 2H), 6.94 (d, J=8.5 Hz, 1H), 7.15–7.22 (m, 2H), 7.22–7.34 (m, 2H), 7.34–7.53 (m, 1H), 7.77–7.85 (m, 1H); HRMS (FAB) Calc'd for M+H: 349.1916, found: 349.1890. Anal. Calc'd for C$_{22}$H$_{24}$N$_2$O$_2$: C, 75.83; H, 6.94; N, 8.04. Found: C, 75.88; H, 6.86; N, 7.85.

EXAMPLE 25

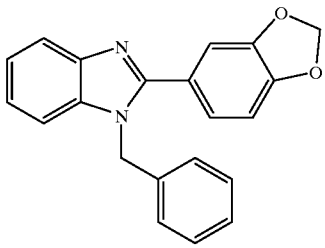

2-(1,3-Benzodioxol-5-yl)-1-phenylmethyl-1H-benzimidazole

Following a procedure similar to the one described in Example 1, with the substitution of benzyl bromide for ethyl 5-bromovalerate (Step 2, Example 1), 2-(1,3-benzodioxol-5-yl)-1-phenylmethyl-1H-benzimidazole was prepared from 2-(1,3-benzodioxol-5-yl)-1H-benzimidazole (Step 1, Example 1) as a white solid: mp 143.2–145.0° C.; $^1$H NMR (CDCl$_3$) δ 5.46 (s, 2H), 6.02 (s, 2H), 6.87 (d, J=8.0 Hz, 1H), 7.05–7.14 (m, 2H), 7.14–7.25 (m, 4H), 7.28–7.40 (m, 4H), 7.87 (d, J=7.9 Hz, 1H); HRMS (FAB) Calc'd for M+H: 329.1290, found: 329.1303. Anal. Calc'd for (C$_{21}$H$_{16}$N$_2$O$_2$+0.16 CH$_2$Cl$_2$]: C, 74.37; H, 4.81; N, 8.20. Found: C, 74.71; H, 4.66; N, 7.95.

EXAMPLE 26

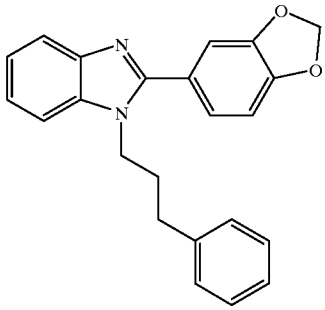

2-(1,3-Benzodioxol-5-yl)-1-(3-phenylpropyl)-1H-benzimidazole

Following a procedure similar to the one described in Example 1, with the substitution of phenylpropyl bromide for ethyl 5-bromovalerate (Step 2, Example 1), 2-(1,3-benzodioxol-5-yl)-1-(3-phenylpropyl)-1H-benzimidazole was prepared from 2-(1,3-benzodioxol-5-yl)-1H-benzimidazole (Step 1, Example 1) as a white solid: mp 99.8–100.5° C.; $^1$H NMR (CDCl$_3$) δ 2.17 (quintet, J=7.7 Hz, 2H), 2.62 (t, J=7.3 Hz, 2H), 4.25 (t, J=7.3 Hz, 2H), 6.07 (s, 2H), 6.88 (d, J=8.1 Hz, 1H), 7.08–7.37 (m, 10H), 7.82–7.90 (m, 1H); HRMS (FAB) Calc'd for M+H: 357.1603, found: 357.1626. Anal. Calc'd for [C$_{23}$H$_{20}$N$_2$O$_2$+0.04 CH$_2$Cl$_2$]: C, 76.86; H, 5.62; N, 7.78. Found: C, 76.87; H, 5.21; N, 7.83.

EXAMPLE 27

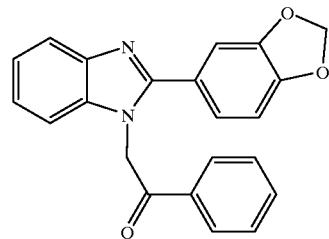

2-[2-(1,3-Benzodioxol-5-yl)-1H-benzimidazol-1-yl]-1-phenylethanone

Following a procedure similar to the one described in Example 1, with the substitution of 2-bromoacetophenone for ethyl 5-bromovalerate (Step 2, Example 1), 2-[2-(1,3-benzodioxol-5-yl)-1H-benzimidazol-1-yl]-1-phenylethanone was prepared from 2-(1,3-benzodioxol-5-yl)-1H-benzimidazole (Step 1, Example 1) as a white solid: mp 186.2–189.0° C.; $^1$H NMR (CDCl$_3$) δ 5.62 (s, 2H), 6.01 (s, 2H), 6.85 (d, J=7.9 Hz, 1H), 7.05–7.20 (m, 2H), 7.25–7.42 (m, 2H), 7.50–7.52 (m, 2H), 7.65–7.73 (m, 2H), 7.86 (d, J=7.3 Hz, 1H), 8.02 (d, J=7.9 Hz, 2H); HRMS (FAB) Calc'd for M+H: 357.1239, found: 357.1211. Anal. Calc'd for [C$_{22}$H$_{16}$N$_2$O$_3$+0.03 CH$_2$Cl$_2$]: C, 73.76; H, 4.51; N, 7.81. Found: C, 73.81; H, 4.66; N, 7.35.

EXAMPLE 28

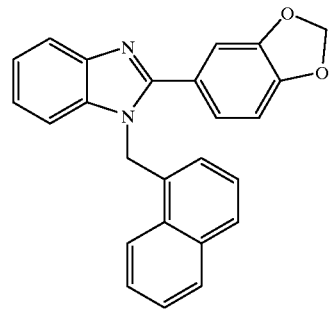

2-(1,3-Benzodioxol-5-yl)-1-(1-naphthalenylmethyl)-1H-benzimidazole

Following a procedure similar to the one described in Example 1, with the substitution of 1-(bromomethyl)naphthalene for ethyl 5-bromovalerate (Step 2, Example 1), 2-(1,3-benzodioxol-5-yl)-1-(1-naphthalenylmethyl)-1H-benzimidazole was prepared from 2-(1,3-benzodioxol-5-yl)-1H-benzimidazole (Step 1, Example 1) as a white solid: mp 166.5–168.0° C.; $^1$H NMR (CDCl$_3$) δ 5.91 (s, 2H), 5.98 (s, 2H), 6.77 (d, J=8.1 Hz, 1H), 6.92 (d, J=6.3 Hz, 1H), 7.10–7.29 (m, 4H), 7.32 (d, J=7.4 Hz, 1H), 7.37 (d, J=7.7 Hz, 1H), 7.57–7.68 (m, 2H), 7.85 (d, J=8.4 Hz, 1H), 7.90 (d, J=8.1 Hz, 1H), 7.93–8.04 (m, 2H); HRMS (FAB) Calc'd M+H: 379.1447, found: 379.1470. Anal. Calc'd for [C$_{25}$H$_{18}$N$_2$O$_2$+0.46 C$_4$H$_6$O$_1$]: C, 78.15; H, 5.52; N, 6.79. Found: C, 78.01; H, 4.94; N, 6.39.

EXAMPLE 29

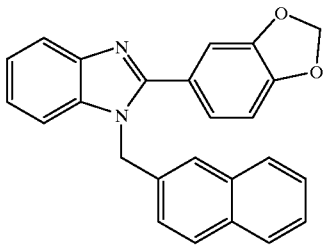

2-(1,3-Benzodioxol-5-yl)-1-(2-naphthalenylmethyl)-1H-benzimidazole

Following a procedure similar to the one described in Example 1, with the substitution of 2-(bromomethyl) naphthalene for ethyl 5-bromovalerate (Step 2, Example 1), 2-(1,3-benzodioxol-5-yl)-1-(2-naphthalenylmethyl)-1H-benzimidazole was prepared from 2-(1,3-benzodioxol-5-yl)-1H-benzimidazole (Step 1, Example 1) as a white solid: mp 179.5–180.4° C.; $^1$H NMR (CDCl$_3$) δ 5.61 (s, 2H), 6.01 (s, 2H), 6.84 (d, J=8.0 Hz, 1H), 7.15–7.38 (m, 6H), 7.43–7.54 (m, 3H), 7.67–7.75 (m, 1H), 7.80–7.92 (m, 3H); HRMS (FAB) Calc'd for M+H: 379.1447, found: 379.1476. Anal. Calc'd for [C$_{25}$H$_{18}$N$_2$O$_2$+0.12 CH$_2$Cl$_2$]: C, 77.62; H, 4.73; N, 7.21. Found: C, 77.62; H, 4.83; N, 7.20.

EXAMPLE 30

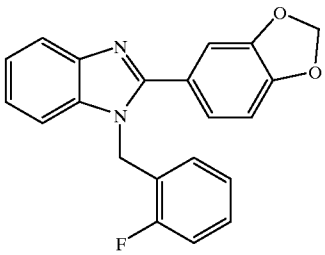

2-(1,3-Benzodioxol-5-yl)-1-(2-fluorophenylmethyl)-1H-benzimidazole

Following a procedure similar to the one described in Example 1, with the substitution of 2-fluorobenzyl bromide for ethyl 5-bromovalerate (Step 2, Example 1), 2-(1,3-benzodioxol-5-yl)-1-(2-fluorophenylmethyl)-1H-benzimidazole was prepared from 2-(1,3-benzodioxol-5-yl)-1H-benzimidazole (Step 1, Example 1) as a white solid: mp 149.0–149.8° C.; $^1$H NMR (CDCl$_3$) δ 5.50 (s, 2H), 6.04 (s, 2H), 6.80 (d, J=7.4 Hz, 1H), 6.88 (d, J=8.0 Hz, 1H), 7.03 (t, J=7.5 Hz, 1H), 7.08–7.39 (m, 7H), 7.85 (d, J=7.8 Hz, 1H); HRMS (FAB) Calc'd for M+H: 347.1196, found: 347.1204. Anal. Calc'd for [C$_{21}$H$_{15}$N$_2$O$_2$F$^+$ 0.08 CH$_2$Cl$_2$]: C, 71.74; H, 4.33; N, 7.94. Found: C, 71.75; H, 4.33; N, 7.90.

EXAMPLE 32

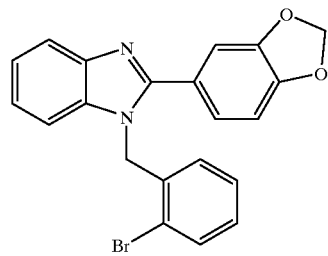

2-(1,3-Benzodioxol-5-yl)-1-(2-bromophenylmethyl)-1H-benzimidazole

Following a procedure similar to the one described in Example 1, with the substitution of 2-bromobenzyl bromide for ethyl 5-bromovalerate (Step 2, Example 1), 2-(1,3-benzodioxol-5-yl)-1-(2-bromophenylmethyl)-1H-benzimidazole was prepared from 2-(1,3-benzodioxol-5-yl)-1H-benzimidazole (Step 1, Example 1) as a white solid: mp 121.8–123.5° C.; $^1$H NMR (CDCl$_3$) δ 5.46 (s, 2H), 6.03 (s, 2H), 6.74 (dd, J=5.8, 3.6 Hz, 1H), 6.86 (d, J=8.1 Hz, 1H), 7.05–7.30 (m, 6H), 7.33 (t, J=7.5 Hz, 1H), 7.63–7.73 (m, 1H), 7.88 (d, J=7.9 Hz, 1H); HRMS (FAB) Calc'd for M+H: 407.0395, found: 407.0436. Anal. Calc'd for [C$_{21}$H$_{15}$N$_2$O$_2$Br$^+$ 0.2 CH$_2$Cl$_2$]: C, 59.98; H, 3.66; N, 6.60. Found: C, 59.98; H, 3.60; N, 6.59.

EXAMPLE 33

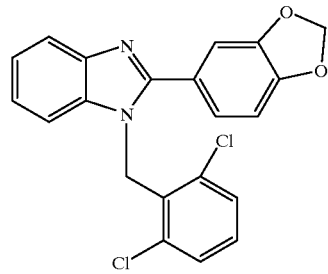

2-(1,3-Benzodioxol-5-yl)-1-(2,6-dichlorophenylmethyl)-1H-benzimidazole

Following a procedure similar to the one described in Example 1, with the substitution of 2,6-dichlorobenzyl bromide for ethyl 5-bromovalerate (Step 2, Example 1), 2-(1,3-benzodioxol-5-yl)-1-(2,6-dichlorophenylmethyl)-1H-benzimidazole was prepared from 2-(1,3-benzodioxol-5-yl)-1H-benzimidazole (Step 1, Example 1) as a white solid: mp 187.2–189.0° C.; $^1$H NMR (CDCl$_3$) δ 5.74 (s, 2H), 6.06 (s, 2H), 6.95 (d, J=8.5 Hz, 1H), 7.01 (d, J=7.9 Hz, 1H), 7.09 (td, J=8.2, 1.1 Hz, 1H), 7.28–7.45 (m, 6H), 7.77 (d, J=8.0 Hz, 1H); HRMS (FAB) Calc'd for M+H: 397.0511, found: 397.0564. Anal. Calc'd for [C$_{21}$H$_{14}$N$_2$O$_2$Cl$_2$$^+$ 0.04 CH$_2$Cl$_2$]: C, 63.06; H, 3.54; N, 6.99; Cl, 18.42. Found: C, 62.82; H, 3.47; N, 7.00; Cl, 18.24.

EXAMPLE 34

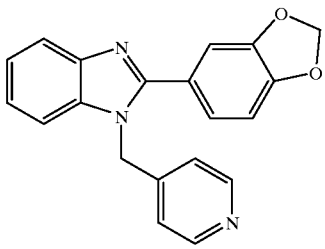

2-(1,3-Benzodioxol-5-yl)-1-(4-pyridinylmethyl)-1H-benzimidazole

Following a procedure similar to the one described in Example 1, with the substitution of 4-picolyl chloride for ethyl 5-bromovalerate (Step 2, Example 1), 2-(1,3-benzodioxol-5-yl)-1-(4-pyridinylmethyl)-1H-benzimidazole was prepared from 2-(1,3-benzodioxol-5-yl)-1H-benzimidazole (Step 1, Example 1) as a white solid: mp 165.5–166.8° C.; $^1$H NMR (CDCl$_3$) δ 5.45 (s, 2H), 6.04 (s, 2H), 6.87 (d, J=8.0 Hz, 1H), 7.00–7.20 (m, 5H), 7.22–7.40 (m, 2H), 7.87 (t, J=7.9 Hz, 1H), 8.55–8.65 (m, 2H); HRMS (FAB) Calc'd for M+: 329.1164, found: 329.1163. Anal. Calc'd for [C$_{20}$H$_{15}$N$_3$O$_2$$^+$ 0.06 CH$_2$Cl$_2$]: C, 72.27; H, 4.27; N, 12.61. Found: C, 72.26; H, 4.53; N, 12.63.

EXAMPLE 35

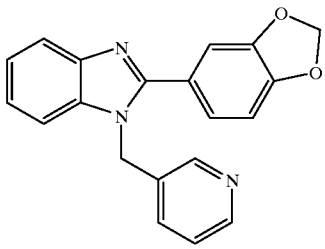

2-(1,3-Benzodioxol-5-yl)-1-(3-pyridinylmethyl)-1H-benzimidazole

Following a procedure similar to the one described in Example 1, with the substitution of 3-picolyl chloride for ethyl 5-bromovalerate (Step 2, Example 1), 2-(1,3-benzodioxol-5-yl)-1-(3-pyridinylmethyl)-1H-benzimidazole was prepared from 2-(1,3-benzodioxol-5-yl)-1H-benzimidazole (Step 1, Example 1) as a white solid: mp 151.5–153.0° C.; $^1$H NMR (CDCl$_3$) δ 5.47 (s, 2H), 6.03 (s, 2H), 6.88 (d, J=8.0 Hz, 1H), 7.05–7.47 (m, 7H), 7.84 (d, J=7.6 Hz, 1H), 8.48 (d, J=1.6 Hz, 1H), 8.55 (dd, J=4.7, 1.6 Hz, 2H); HRMS (FAB) Calc'd for M+H: 330.1243, found: 330.1270. Anal. Calc'd for [C$_{20}$H$_{15}$N$_3$O$_2$$^+$ 0.12 CH$_2$Cl$_2$]: C, 71.12; H, 4.52; N, 12.36. Found: C, 71.11; H, 4.51; N, 12.43.

EXAMPLE 36

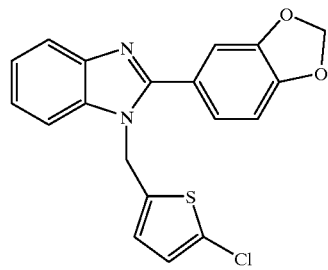

2-(1,3-Benzodioxol-5-yl)-1-[(5-chlorothien-2-yl)methyl]-1H-benzimidazole

Following a procedure similar to the one described in Example 1, with the substitution of 2-chloro-5-(chloromethyl)thiophene for ethyl 5-bromovalerate (Step 2, Example 1), 2-(1,3-benzodioxol-5-yl)-1-[(5-chlorothien-2-yl)methyl]-1H-benzimidazole was prepared from 2-(1,3-benzodioxol-5-yl)-1H-benzimidazole (Step 1, Example 1) as a white solid: mp 129.9–131.2° C.; $^1$H NMR (CDCl$_3$) δ 5.46 (s, 2H), 6.07 (s, 2H), 6.63 (d, J=3.8 Hz, 1H), 6.76 (d, J=3.8 Hz, 1H), 6.94 (d, J=8.7 Hz, 1H), 7.20 (d, J=1.7 Hz, 1H), 7.18–7.25 [m (with d at 7.20, J=1.7 Hz, and s at 7.22), 2H], 7.28–7.40 (m, 3H), 7.78–7.87 (m, 1H); HRMS (FAB) Calc'd for M+H: 369.0465, found: 369.0518. Anal. Calc'd for C$_{19}$H$_{13}$N$_2$O$_2$SCl: C, 61.87; H, 3.55; N, 7.60; S, 8.69. Found: C, 61.74; H, 3.31; N, 7.52; S, 8.83.

EXAMPLE 37

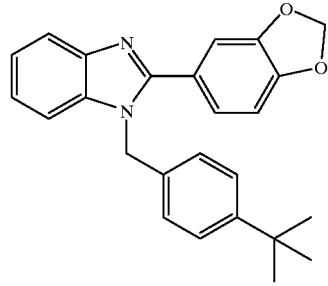

2-(1,3-Benzodioxol-5-yl)-1-[4-(1,1-dimethylethyl)-phenylmethyl]-1H-benzimidazole Following a procedure similar to the one described in Example 1, with the substitution of 4-(tert-butyl)benzyl bromide for ethyl 5-bromovalerate (Step 2, Example 1), 2-(1,3-benzodioxol-5-yl)-1-[4-(1,1-dimethylethyl)-phenylmethyl]-1H-benzimidazole was prepared from 2-(1,3-benzodioxol-5-yl)-1H-benzimidazole (Step 1, Example 1) as a white solid: mp 141.8–143.5° C.; $^1$H NMR (CDCl$_3$) δ 1.30 (s, 9H), 5.42 (s, 2H), 6.02 (s, 2H), 6.87 (d, J=8.0 Hz, 1H), 7.03 (d, J=8.4 Hz, 2H), 7.15–7.40 [m (with d at 7.33, J=8.4 Hz), 7H], 7.83 (d, J=7.9 Hz, 1H); HRMS (FAB) Calc'd for M+H: 385.1916, found: 385.1946. Anal. Calc'd for [C$_{25}$H$_{24}$N$_2$O$_2$$^+$ 0.2 CH$_2$Cl$_2$]: C, 75.45; H, 6.13; N, 6.98. Found: C, 75.45; H, 6.16; N, 7.00.

EXAMPLE 38

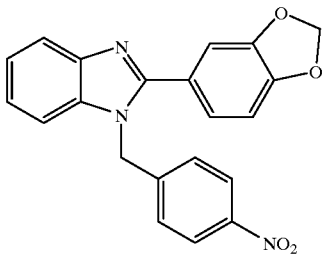

2-(1,3-Benzodioxol-5-yl)-1-(4-nitrophenylmethyl)-1H-benzimidazole

Following a procedure similar to the one described in Example 1, with the substitution of 4-nitrobenzyl chloride for ethyl 5-bromovalerate (Step 2, Example 1), 2-(1,3-benzodioxol-5-yl)-1-(4-nitrophenylmethyl)-1H-benzimidazole was prepared from 2-(1,3-benzodioxol-5-yl)-1H-benzimidazole (Step 1, Example 1) as a white solid: mp 171.5–173.5° C.; $^1$H NMR (CDCl$_3$) δ 5.54 (s, 2H), 6.05 (s, 2H), 6.89 (d, J=8.1 Hz, 1H), 7.10 (dd, J=7.8, 1.8 Hz, 1H), 7.12–7.20 [m (with d at 7.13, J=1.8 Hz), 2H], 7.20–7.40 (m, 3H), 7.51 (t, J=8.1 Hz, 1H), 7.87 (d, J=7.8 Hz, 1H), 8.04 (s, 1H), 8.17 (d, J=8.1 Hz, 1H); HRMS (FAB) Calc'd for M+H: 374.1141, found: 374.1144. Anal. Calc'd for [C$_{21}$H$_{15}$N$_3$O$_4^+$ 0.1 CH$_2$Cl$_2$]: C, 66.32; H, 4.01; N, 10.99. Found: C, 66.34; H, 3.96; N, 10.89.

EXAMPLE 39

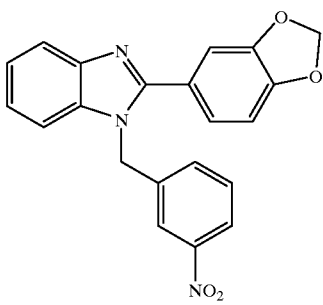

2-(1,3-Benzodioxol-5-yl)-1-(3-nitrophenylmethyl)-1H-benzimidazole

Following a procedure similar to the one described in Example 1, with the substitution of 3-nitrobenzyl chloride for ethyl 5-bromovalerate (Step 2, Example 1), 2-(1,3-benzodioxol-5-yl)-1-(3-nitrophenylmethyl)-1H-benzimidazole was prepared from 2-(1,3-benzodioxol-5-yl)-1H-benzimidazole (Step 1, Example 1) as a white solid: mp 70.2–73.0° C.; $^1$H NMR (CDCl$_3$) δ 5.54 (s, 2H), 6.03 (s, 2H), 6.86 (d, J=8.0 Hz, 1H), 7.04–7.16 (m, 3H), 7.20–7.30 (m, 3H), 7.33 (t, J=7.5 Hz, 1H), 7.86 (d, J=7.9 Hz, 1H), 8.20 (d, J=8.8 Hz, 2H); HRMS (FAB) Calc'd for M+H: 374.1141, found: 374.1119. Anal. Calc'd for [C$_{21}$H$_{15}$N$_3$O$_4^+$ 0.19 CH$_2$Cl$_2$]: C, 65.38; H, 3.98; N, 10.80. Found: 65.41; H, 3.98; N, 10.67.

EXAMPLE 40

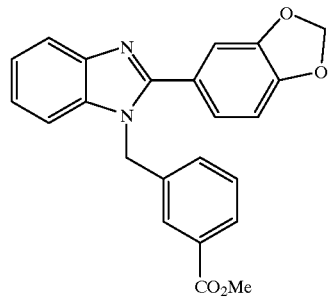

Methyl 3-[[2-(1,3-benzodioxol-5-yl)-1H-benzimidazol-5-yl]methyl]benzoate

Following a procedure similar to the one described in Example 1, with the substitution of methyl 3-bromomethylbenzoate for ethyl 5-bromovalerate (Step 2, Example 1), methyl 3-[[2-(1,3-benzodioxol-5-yl)-1H-benzimidazol-5-yl]methyl]benzoate was prepared from 2-(1,3-benzodioxol-5-yl)-1H-benzimidazole (Step 1, Example 1) as a white solid: mp 122.2–124.1° C.; $^1$H NMR (CDCl$_3$) δ 3.89 (s, 3H), 5.48 (s, 2H), 6.02 (s, 2H), 6.86 (d, J=8.0 Hz, 1H), 7.08–7.33 (m, 6H), 7.39 (t, J=7.8 Hz, 1H), 7.80–7.92 (m, 2H), 7.98 (d, J=7.7 Hz, 1H); HRMS (FAB) Calc'd for M+H: 387.1345, found: 387.1323. Anal. Calc'd for [C$_{23}$H$_{18}$N$_2$O$_4$: C, 71.49; H, 4.70; N, 7.25. Found: C, 71.20; H, 4.68; N, 7.15.

EXAMPLE 41

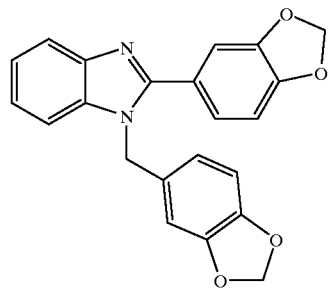

2-(1,3-Benzodioxol-5-yl)-1-[(1,3-benzodioxol-5-yl)methyl]-1H-benzimidazole

Following a procedure similar to the one described in Example 1, with the substitution of 3,4-methylenedioxybenzyl chloride for ethyl 5-bromovalerate (Step 2, Example 1), 2-(1,3-benzodioxol-5-yl)-1-[(1,3-benzodioxol-5-yl)methyl]-1H-benzimidazole was prepared from 2-(1,3-benzodioxol-5-yl)-1H-benzimidazole (Step 1, Example 1) as a white solid: mp 173.0–173.8° C.; $^1$H NMR (CDCl$_3$) δ 5.36 (s, 2H), 5.95 (s, 2H), 6.04 (s, 2H), 6.53–6.68 (m, 2H), 6.75 (d, J=8.4 Hz, 1H), 6.89 (d, J=8.0 Hz, 1H), 7.15–7.40 (m, 5H), 7.83 (d, J=7.8 Hz, 1H); HRMS (EI) Calc'd for M+H: 373.1188, found: 373.1196. Anal. Calc'd for C$_{21}$H$_{16}$N$_2$O$_4$: C, 70.96; H, 4.33; N, 7.52. Found: C, 70.86; H, 4.38; N, 7.55.

EXAMPLE 42

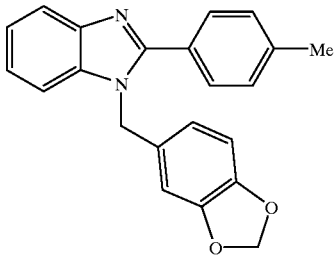

1-[(1,3-benzodioxol-5-yl)methyl]-2-(4-methylphenyl)-1H-benzimidazole

Following a procedure similar to the one described in Example 1 (Step 1), with the substitution of p-tolualdehyde for piperonal, 2-(4-methylphenyl)-1H-benzimidazole was prepared and used directly in the next step without characterization.

Following a procedure similar to the one described in Example 1 (Step 2), with the substitution of 3,4-methylenedioxybenzyl chloride for ethyl 5-bromovalerate (Step 2, Example 1), 1-[(1,3-benzodioxol-5-yl)methyl]-2-(4-methylphenyl)-1H-benzimidazole was prepared from 2-(4-methylphenyl)-1H-benzimidazole from above as a white solid: mp 99.1–101.3° C.; $^1$H NMR (CDCl$_3$) δ 2.43 (s, 3), 5.36 (s, 2H), 5.95 (s, 2H), 6.55–6.62 (m, 2H), 6.76 (d, J=8.4 Hz, 1H), 7.20–7.35 (m, 5H), 7.60 (d, J=8.2 Hz, 2H), 7.86 (d, J=7.8 Hz, 1H); HRMS (EI) Calc'd for M+H: 343.1447, found: 343.1487. Anal. Calc'd for [C$_{22}$H$_{18}$N$_2$O$_2$+ 0.12 CH$_2$Cl$_2$]: C, 75.32; H, 5.21; N, 7.94. Found: C, 75.35; H, 4.91; N, 7.83.

EXAMPLE 43

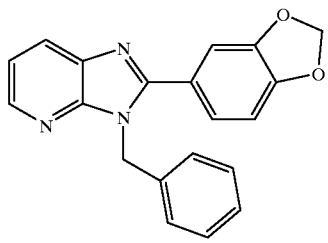

2-(1,3-Benzodioxol-5-yl)-3-(phenylmethyl)-3H-imidazo[4,5-b]pyridine

Following a procedure similar to the one described in Example 1 (Step 1), with the substitution of 2,3-diaminopyridine for phenylenediamine, 2-(1,3-benzodioxol-5-yl)-3H-imidazo[4,5-b]pyridine was prepared as a light brown solid which was used directly in the next step.

Following a procedure similar to the one described in Example 1 (Step 2), with the substitution of benzyl bromide for ethyl 5-bromovalerate, 2-(1,3-benzodioxol-5-yl)-3-(phenylmethyl)-3H-imidazo[4,5-b]pyridine was prepared from 2-(1,3-benzodioxol-5-yl)-3H-imidazo[4,5-b]pyridine (from above) as a solid: $^1$H NMR (CDCl$_3$) δ 5.60 (s, 2H), 6.03 (s, 2H), 6.86 (d, J=8.6 Hz, 1H), 7.07–7.20 (m, 4H), 7.25–7.35 (m, 4H), 8.09 (dd, J=8.0, 1.4 Hz, 1H), 8.40 (dd, J=4.8, 1.4 Hz, 1H); HRMS (FAB) Calc'd for M+H: 330.1243, found: 330.1295. Anal. Calc'd for [C$_{20}$H$_{15}$N$_3$O$_2$+ 0.1 CH$_2$Cl$_2$]: C, 71.43; H, 4.53; N, 12.43. Found: C, 71.50; H, 4.71; N, 12.10.

EXAMPLE 44

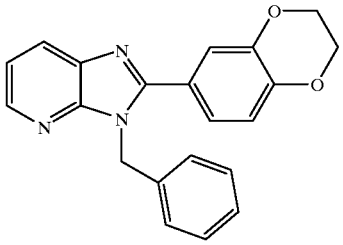

2-(2,3-Dihydro-1,4-benzodioxin-6-yl)-3-(phenylmethyl)-3H-imidazo[4,5-b]pyridine Step 1: Preparation of 2-(2,3-dihydro-1,4-benzodioxin-6-yl)-3H-imidazo[4,5-b]pyridine Following a procedure similar to the one described in Example 1 (Step 1), with the substitution of 1,4-benzodioxan-6-carboxaldehyde for piperonal, 2-(2,3-dihydro-1,4-benzodioxin-6-yl)-3H-imidazo[4,5-b]pyridine was prepared as a solid: $^1$H NMR (DMSO, d$_6$) δ 4.33 (s, 4H), 7.05 (t, J=9.01 Hz, 1H), 7.26–7.28 (m, 1H), 7.68–7.78 (m, 4H), 8.00 (md, J=7.03 Hz, 1H), 8.28 (dd, J=3.6, 1.0 Hz, 1H).

Step 2: Preparation of 2-(2,3-dihydro-1,4-benzodioxin-6-yl)-3-(phenylmethyl)-3H-imidazo[4,5-b]pyridine Following a procedure similar to the one described in Example 1 (Step 2), with the substitution of benzyl bromide for ethyl 5-bromovalerate, 2-(2,3-dihydro-1,4-benzodioxin-6-yl)-3-(phenylmethyl)-3H-imidazo[4,5-b]pyridine was prepared from 2-(2,3-dihydro-1,4-benzodioxin-6-yl)-3H-imidazo[4,5-b]pyridine (from Step 1) as a solid: mp 156.5–157.5° C.; $^1$H NMR (DMSO, d$_6$) δ 4.20–4.40 (m, 4H), 5.63 (s, 2H), 6.95–7.05 (m, 3H), 7.20–7.40 (m, 6H), 8.12 (dd, J=8.0, 1.3 Hz, 1H),8.34 (dd, J=4.7, 1.3 Hz, 1H); HRMS (FAB) Calc'd for M+H: 344.1399, found: 344.1433. Anal. Calc'd for [C$_{21}$H$_{17}$N$_3$O$_2$+0.13 CH$_2$Cl$_2$]: C, 71.56; H, 4.91; N, 11.85. Found: C, 71.55; H, 4.99; N, 11.88.

ISOLATION OF PHOSPHODIESTERASE ENZYMES

Phosphodiesterase enzymes were partially purified according to the procedures reported by Francis, S. H., and Corbin, J. D. (1988) in *Methods in Enzymology*, Vol. 159, pp. 722–729, Academic Press, New York and Bradford, M. M. in (1976) *Anal. Biochem.* 72, 248–254. Specifically, the purification was accomplished by chromatography of a bovine aorta extract on a DEAE Tris-acryl column. The eluted fractions were assayed for the various specific activities. The specific enzyme activities were pooled and concentrated. This procedure resulted in enzyme activities which were essentially free of cross contaminating phosphodiesterase activity. The cGMP-specific phosphodiesterase was assayed in the presence of 1 μM cGMP. The calcium/calmodulin dependent enzyme activity was assayed in the presence of 1 μM cGMP, 0.5 units calmodulin (Sigma P-0270, phosphodiesterase 3',5'-cyclic nucleotide activator from bovine heart) per ml of reaction, and 100 μM Ca$^{2+}$.

The partially purified cGMP-specific PDE from bovine aorta was stored as a concentrated solution in glycerol at 4° C. Prior to use it was diluted approximately 1:3000 with an assay buffer containing 100 mM Tris-HCl and 5 mM MgSO$_4$ at pH 7.5 to give approximately 10% conversion of cGMP substrate to GMP in a 30 minute reaction time.

ASSAY FOR INHIBITION OF cGMP PDE

Enzyme assays were performed in Millipore 96-well polystyrene microtiter plates in a total assay volume of 100

μL of buffer containing 100 mM Tris-HCl and 5 mM MgSO$_4$ at pH 7.5. cGMP PDE inhibitor compounds were dissolved in DMSO at a concentration of 10 mM and then diluted into the assay to give a final concentration of DMSO in the assay of 1% which has no effect on the enzymatic reaction. The reaction mixture consisted of 10 μL diluted inhibitor, 10 μL of a solution of the appropriate phosphodiesterase enzyme preparation, and 60 μL buffer. The reaction was initiated by the addition 20 μL of 5μM [3H]cGMP (100,000 DPM/well). The tritiated cGMP nucleotides were obtained from DuPont/New England Nuclear Lifesciences Company, Boston, Mass. as an ammonium salt (NET-554 guanosine 3',5'-cyclic phosphate, [8,5'-$^3$H]).

After a 30 minute incubation at room temperature the reaction was stopped by the addition of 50 μL of 210 mM ZnSO$_4$ followed by an addition of 50 μL of freshly prepared 19 mM Ba(OH)$_2$ to specifically precipitate the radiolabled 5'-nucleotide product. The Zn—Ba precipitate was filtered onto glass-fiber filters mats (Wallac, Filtermat A, 102×258 mm) using an automated 96-well harvester (TOMTEC Harvester 96®, MACH II). The precipitate was washed from the microtiterplate to the filtermat with a total volume of 1 ml/well of a wash buffer containing 1 mM NaOH and 100 mM NaCl. The filtermat were dried in a microwave oven and placed in a Wallac sample bag for use with the 1205 BetaPlate™. 10 ml of Beta Plate Scint (LKB) was added to the bag and allowed to diffuse throughout the filter. The radiolabel was then quantitated using a LKB/Wallac 1205 BetaPlate™ scintillation counter. Inhibitor dilution curves were created using six concentrations of the inhibitor in duplicate. IC$_{50}$ values were determined from a linear regression of a Log Logit transformation of the data. M&B 22,948 (2-o-propoxyphenyl-8-azapurin-6-one) was used as the standard control inhibitor for cGMP PDE and was prepared according to U.S. Pat. No. 3,819,631.

ASSAY FOR INHIBITION OF cAMP PDE

The procedure for the inhibition of cAMP PDE was identical to the procedure for the cGMP-specific phosphodiesterase assay above, except that partially purified cAMP PDE from bovine aorta was collected as pooled from the DEAE tris-acryl column based upon its elution relative to cGMP-specific PDE as well as its specificity for cAMP by hydrolysis and then used. The partially purified cAMP PDE was stored as a concentrated solution at 4° C. This enzyme was diluted 1:30 with an assay buffer prior to use. A substrate solution of [$^3$H]cAMP was added to 5 μM adenosine 3', 5'-cyclic monophosphate sodium salt in assay buffer to give a solution with a specific activity of 1000 CPM/pmole (100,000 CPM/20 μl). The reaction was initiated by the addition 20 μL of 5 μM [3H]cAMP (100,000 DPM/well). The tritiated cAMP nucleotides were obtained from DuPont/New England Nuclear Lifesciences Company, Boston, Mass. as an ammonium salt (NET-275 adenosine 3',5'-cyclic phosphate, (2,8-$^3$H]). Ro 20-1724 was used as the standard control (obtained from Hoffmann LaRoche, Nutley, N.J.).

ASSAY FOR INHIBITION OF CALCIUM/CALMODULIN DEPENDENT cGMP PHOSPHODIESTERASE ENZYME ("Ca PDE")

The procedure for the calcium/calmodulin dependent cGMP PDE assay was identical to the cGMP-specific phosphodiesterase assay described above, except for the following changes noted below. Partially purified ca/calmodulin dependent cGMP PDE enzyme from bovine aorta was collected as a pool based upon its elution relative to cAMP-dependent PDE and conformational changes introduced by the addition of 1 mM EDTA for 1 hour at 4° C. It was then diluted 1:1800 in assay buffer containing 143 μM CaCl$_2$ and 0.7 units of calmodulin/ml and 70 μl of this enzyme solution was used per assay well. The standard control used was Vinpocetine purchased from Gedeon Richter LTD, Budapest, Hungary.

The following table lists the IC$_{50}$ values for the inhibition of phosphodiesterase enzymes by the compounds described herein. Values reported are averaged where multiple testing was performed.

| Example No. | cGMP PDE IC$_{50}$ (μM) | cAMP PDE IC$_{50}$ (μM) | Ca GMP PDE IC$_{50}$ (μM) |
| --- | --- | --- | --- |
| 41 | 0.003 | 11.9 | 64.5 |
| 43 | 0.003 | 7.3 | >100 |
| 42 | 0.009 | 18 | 60 |
| 30 | 0.004 | >100 | >100 |
| 25 | 0.011 | 12.4 | 75 |
| 29 | 0.024 | 5.2 | 60 |

IN VIVO METHODS FOR MEASURING CARDIOVASCULAR EFFECTS

Inhibition of cGMP-specific PDE results in an increase in intracellular cGMP levels. Since cGMP mediates the smooth muscle relaxing effects of a number of physiological agents, i.e., atriopeptin, nitric oxide and other nitrovasodilators, an inhibition of cGMP-PDE in the vascular smooth musculature can reasonably be expected to cause vasorelaxation and a reduction in systemic blood pressure. McMahon et al. have shown that the administration of the selective cGMP-PDE inhibitor, M&B 22,948 causes a dose-dependent reduction in the mean arterial pressure in rats, and moreover, this reduction is accompanied by an increase in urinary cGMP (and not cAMP) levels (E. G. McMahon et al., *J. Pharmacol. Exp. Ther.* 251, 1000–1005, 1989).

Polyethylene catheters (PE50) were inserted into the femoral artery and vein of anesthetized male Sprague Dawley rats (Charles River Laboratories, Wilmington, Mass.) in order to monitor the mean arterial pressure and administer test compounds. Following surgery, the animals were place in individual restraining cages and allowed to regain consciousness. Infusion of 0.9% sodium chloride via the femoral vein (0.07 ml/kg/min) was begun and continued throughout the study period. Observations were begun approximately 90 minutes after the initiation of infusion to allow the animals to fully regain consciousness. Blood pressure was continuously monitored via the femoral artery with a pressure transducer (type 041-500-503; Cobe, Lakewood, Colo.) connected to a Grass Model 7E polygraph. Mean arterial pressure and heart rates were recorded at 3 minute intervals by a computerized data acquisition system. Cyclic GMP phosphodiesterase inhibitor (Example 41) was administered as an intraperitoneal injection, alternatively the inhibitor could have been administered directly into the catheter as an intravenous bolus. A reduction in blood pressure was observed (see drawing), consistent with the presence of an increase in intracellular cGMP levels due to inhibition of cGMP-specific PDE.

Also embraced within this invention is a class of pharmaceutical compositions comprising one or more compounds of Formulae I–III in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a therapeutically effective amount for the treatment intended.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be-an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Other variations and modifications of this invention will be obvious to those skilled in the art. This invention is not limited except as set forth in the following claims.

What is claimed is:

1. A compound selected from the group of compounds having the following structures:

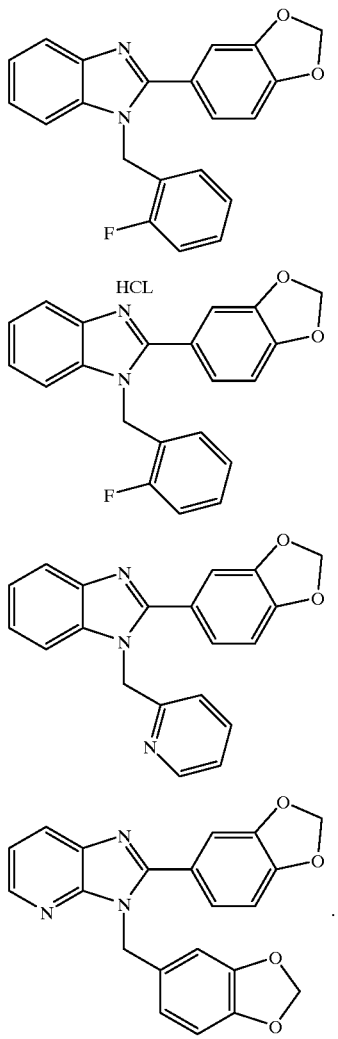

2. A method of treating glaucoma, impotence, asthma and cardiovascular disorders selected from the group consisting of stable-, unstable- and variant-angina, hypertension, pulmonary hypertension, congestive heart failure, atherosclerosis, and thrombosis, which comprises administering a therapeutically effective amount of a compound of Formula II,

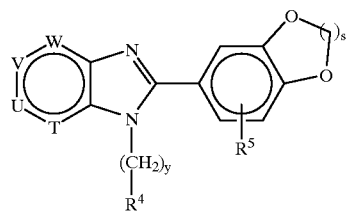

Formula II or a pharmaceutically acceptable salt thereof;

wherein y is an integer from 0 to 6;

wherein s is an integer from 1 to 3;

wherein $R^4$ is selected from the group consisting of alkyl, alkoxyalkyl, carboxyalkyl, alkylcarbonyl, arylcarbonyl, alkoxycarbonyl, alkenyl, alkoxyalkenyl, alkynyl, alkoxyalkynyl, cycloalkyl, cycloalkenyl, heterocycle, bicyclic aryl, heteroaryl and aryl, which groups are independently unsubstituted or substituted by one or more substituents independently selected from the group consisting of alkyl, alkyl sulfonyl, alkenyl, alkynyl, amino, hydroxy and alkoxy, and wherein bicyclic aryl, aryl and heteroaryl are independently unsubstituted or substituted by one or more substituents independently selected from the group consisting of halo, nitro, alkoxycarbonyl and —O—$(CH_2)_p$—O—, wherein p is an integer from 1 to 3 and the oxygen atoms are bonded to adjacent carbons;

wherein $R^5$ is selected from the group consisting of hydrido, hydroxy, halo, nitro, alkyl, alkyl sulfonyl, alkoxy, alkenyl, alkynyl and amino; and wherein at least one of T, U, V, and W is $CR^6$ and the remainder are independently N or $CR^6$, wherein each $R^6$ when present is independently selected from the group consisting of hydrido, hydroxy, halo, nitro, alkyl, alkyl sulfonyl, alkoxy, alkenyl, alkynyl and amino.

3. A method of treating glaucoma, impotence, asthma and cardiovascular disorders selected from the group consisting of stable-, unstable- and variant-angina, hypertension, pulmonary hypertension, congestive heart failure, atherosclerosis, and thrombosis, which comprises administering a therapeutically effective amount of a compound of Formula III,

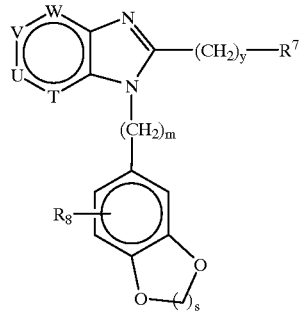

Formula III or a pharmaceutically acceptable salt thereof;

wherein m is an integer from 0 to 3;

wherein y is an integer from 0 to 6;

wherein s is an integer from 1 to 3;

wherein $R^7$ is selected from the group consisting of alkyl, alkoxyalkyl, carboxyalkyl, alkylcarbonyl, arylcarbonyl, alkenyl, alkoxyalkenyl, alkynyl, alkoxyalkynyl, cycloalkyl, cycloalkenyl, heterocycle, bicyclic aryl, heteroaryl and aryl, which groups are independently unsubstituted or substituted by one or more substituents selected from the group consisting of alkyl, alkyl sulfonyl, alkenyl, alkynyl, amino, hydroxy and alkoxy, and wherein bicyclic aryl, aryl and heteroaryl are independently unsubstituted or substituted by one or more substituents selected from the group consisting of halo, nitro, alkoxycarbonyl, and —O—(CH$_2$)$_p$—O—, wherein p is an integer from 1 to 3 and the oxygen atoms are bonded to adjacent carbons;

wherein R$^8$ is selected from the group consisting of hydrido, hydroxy, halo, nitro, alkyl, alkyl sulfonyl, alkoxy, alkenyl, alkynyl and amino; and wherein at least one of T, U, V, and W is CR$^9$ and the remainder are independently N or CR$^9$, wherein each R$^9$ when present is independently selected from the group consisting of hydrido, hydroxy, nitro, alkyl, alkyl sulfonyl, alkoxy, alkenyl, alkynyl and amino.

4. The method of claim 2, wherein the compound has one of the following structures:

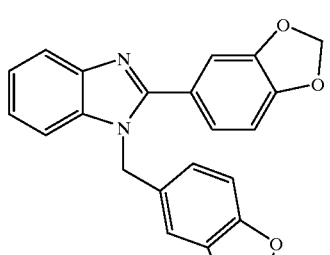

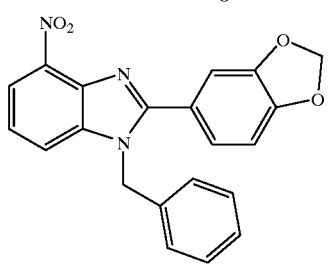

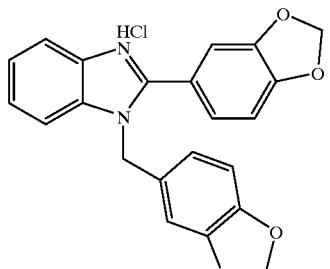

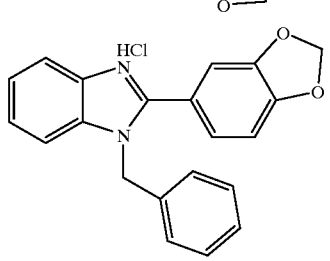

-continued

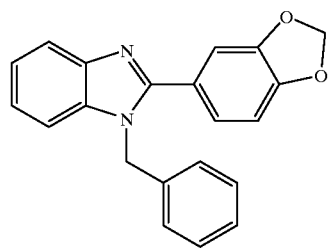

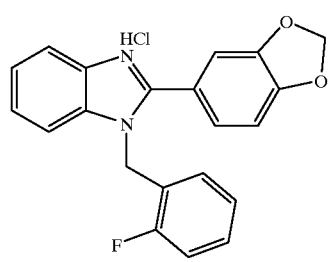

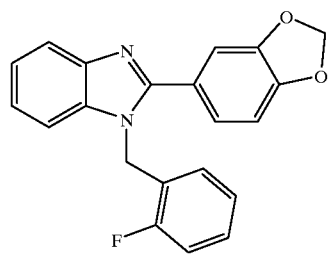

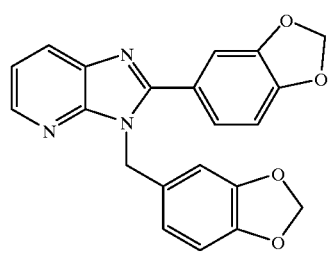

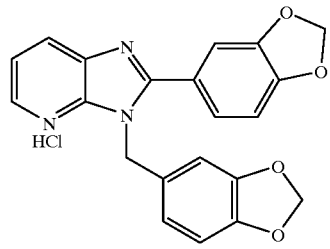

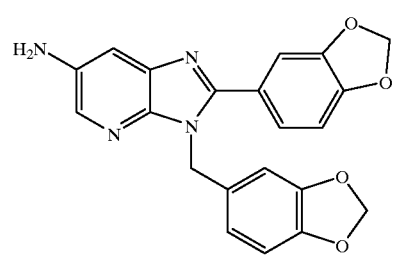

-continued
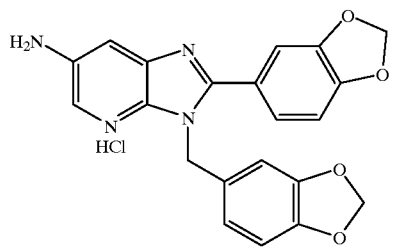
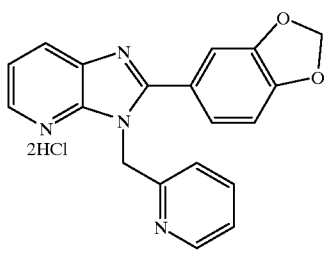
-continued
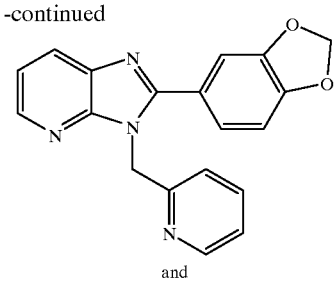
and
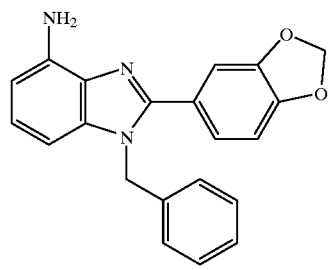
* * * * *

UNITED STATES PATENT AND TRADEMARK OFFICE
CERTIFICATE OF CORRECTION

PATENT NO. : 6,130,333
DATED : October 10, 2000
INVENTOR(S) : Horng-Chih Huang et al.

It is certified that error appears in the above-identified patent and that said Letters Patent is hereby corrected as shown below:

<u>Title page,</u>
Item [56], References Cited,
FOREIGN PATENT DOCUMENTS, "2305339  3/1973  Germany.
                          123 053  11/1976  Germany."

should read
FOREIGN PATENT DOCUMENTS, -- 2 305 339  8/1974 Germany.
                             123 053    6/1900 Germany. --

<u>Column 5,</u>
Line 62, "in vention" should read -- invention --.

<u>Column 11,</u>
Line 6, "cydloalkenyl," should read -- cycloalkenyl, --.

<u>Column 16,</u>
Line 4, "acids;" should read -- acids: --.
Line 16, "pantothenic, benzenesulfonic," should read
-- pantothenic, benzenesulfonic, --.
Line 21, "bases;" should read -- bases: --.
Line 22, "bases;" should read -- bases: --.

<u>Column 38,</u>
Line 32, "[$C_{23}H_{18}N_2O_4$:" should read -- [$C_{23}H_{18}N_2O_4$]: --.

<u>Column 41,</u>
Line 25, "Beta Plate" should read -- BetaPlate --.

UNITED STATES PATENT AND TRADEMARK OFFICE
CERTIFICATE OF CORRECTION

PATENT NO. : 6,130,333
DATED : October 10, 2000
INVENTOR(S) : Horng-Chih Huang et al.

It is certified that error appears in the above-identified patent and that said Letters Patent is hereby corrected as shown below:

Column 42,
Line 39, "place" should read -- placed --.

Column 43,
Line 37, "be-an" should read -- be an --.

Signed and Sealed this

Sixth Day of November, 2001

Attest:

*Nicholas P. Godici*

NICHOLAS P. GODICI
*Attesting Officer*     *Acting Director of the United States Patent and Trademark Office*